United States Patent
Morjana et al.

(10) Patent No.: US 6,248,869 B1
(45) Date of Patent: Jun. 19, 2001

(54) TROPONIN I FORMS AND USE OF THE SAME

(75) Inventors: Nihmat A. Morjana, Pembroke Pines; Angela M. Puia, Miami, both of FL (US)

(73) Assignee: Medical Analysis Systems, Inc., Camarillo, CA (US)

(*) Notice: Subject to any disclaimer, the term of this patent is extended or adjusted under 35 U.S.C. 154(b) by 0 days.

(21) Appl. No.: 08/865,468

(22) Filed: May 29, 1997

(51) Int. Cl.$^7$ .................................................. C07K 13/00

(52) U.S. Cl. ........................... 530/841; 530/350; 514/2; 514/12; 514/21; 436/63; 436/86

(58) Field of Search ................................ 530/350, 841; 514/2, 12, 21; 436/63, 86

(56) References Cited

U.S. PATENT DOCUMENTS

| | | | |
|---|---|---|---|
| 4,105,499 | 8/1978 | Kiyasu | 195/103.5 |
| 4,767,843 | 8/1988 | Yazaki | 530/387 |
| 4,879,216 | 11/1989 | Hallermayer et al. | 435/7 |
| 4,943,427 | 7/1990 | Yazaki et al. | 424/1.1 |
| 5,206,007 | 4/1993 | Ooshima et al. | 424/9 |
| 5,227,307 | 7/1993 | Bar-Or et al. | 436/63 |
| 5,266,488 | 11/1993 | Ordahl et al. | 435/240.2 |
| 5,290,519 | 3/1994 | Bar-Or et al. | 422/61 |
| 5,290,678 | 3/1994 | Jackowski | 435/7.4 |
| 5,418,139 | 5/1995 | Campbell | 435/7.21 |
| 5,449,669 | 9/1995 | Metcalfe et al. | 514/13 |
| 5,498,524 | 3/1996 | Hall | 435/7.1 |
| 5,560,937 | 10/1996 | Lee et al. | 424/569 |
| 5,583,200 | 12/1996 | Larue et al. | 530/350 |
| 5,604,105 | 2/1997 | Jackowski | 435/7.4 |
| 5,925,533 * | 7/1999 | Doth et al. | 435/7.94 |

FOREIGN PATENT DOCUMENTS

| | | |
|---|---|---|
| 0743522A1 | 11/1996 | (EP). |
| 0 752 426 | 1/1997 | (EP). |
| 200 358 | 1/1987 | (GB). |
| 2275 774A | 2/1994 | (GB). |
| WO 94/15217 | 7/1994 | (WO). |
| WO 94/27156 | 11/1994 | (WO). |
| WO 96/10076 | 4/1996 | (WO). |
| WO 96 27661 | 9/1996 | (WO). |
| WO 97 19955 | 6/1997 | (WO). |

OTHER PUBLICATIONS

Rudinger, Peptide Hormones, University Park Press, Jun. 1976, pp. 1–7.*

Cummins, et al., "Immunoassay of the cardiac–specific isoform of troponin–I in the diagnosis of heart muscle damage," Biochemical Society Transactions, vol. 15, No. 6, 1987, p. 1060/1061.

Farah, et al., "The troponin complex and regulation of muscle contraction," The FASEB Journal, 9:755–767, 1995.

Gao, et al., "Role of troponin I in the pathogenesis of stunned myocardium," Circulation Research, vol. 80, No. 3, 1997, pp. 393–399.

Kobayashi, et al., "Extensive interactions between troponins C and I. Zero–length cross–linking of troponin I and acetylated troponin C," Biochemistry, 34:109646–10952 (1995).

Leszyk, et al., "Cross–linking of rabbit skeletal muscle troponin subunits: labeling of cysteine–98 of troponin C with 4–maleimidobenzophenone and analysis of products formed in the binary complex with troponin T and the ternary complex with troponins I and T," Biochemistry, 27:6983–6987 (1988).

Morjana, et al., "Degradation of human cardiac troponin I after myocardial infarction," FASEB Journal, vol. 11, No. 9, p. A998, 1997.

Adams, J. et al., "Cardiac Troponin I A Marker with High Specificity for Cardiac Injury." Circulation, vol. 88, No. 1, 100–106 (Jul. 1993).

Apple, F.S., "Diagnosic markers for Detection of Acute Myocardial Infarction and Reperfusion", Laboratory Medicine vol. 23, No. 5 297–302 (May 1992).

Ball, K. et al., "Isoform Specific Interactions of Troponin I and Troponin C Determine pH Sensitivity of Myofibrillar Ca2 + Activation." Biochemistry, vol. 33, No. 28, 1994, 8464–8471.

Berson, G. et al., Pflugers Arch. 374:277–283, 1978.

Bodor, G.S. et al., Clin. Chem. 38(11):2203–2214, 1992.

Burtnick, L.D. et al., Can. J. Biochem. 53:1207–1213, 1975.

Cheung, H. et al. "Interactions of Troponin Subunits: Free Energy of Binary And Ternary Complexes." Biochemistry, vol. 26, No. 18, 1987.

Cummins, P. et al., Biochem J 171:251–259, 1978.

Cummins, B. et al., Am. Heart J. 113(6):1333–1344, 1987.

F. Di Lisa, et al. Specific Degradation of Troponin T and I by $\mu$–calpain and its Modulation by Substrate Phosphorylation, Biochem. J. (1995) 308. 57–61.

(List continued on next page.)

Primary Examiner—Marianne M. Cintins
Assistant Examiner—C. Delacroix-Muirheid
(74) Attorney, Agent, or Firm—Morrison & Foerster, LLP

(57) ABSTRACT

The present invention relates to an isolated fragment of human cardiac troponin I (TnI) comprising the following sequence

X-A-B-Y wherein

X comprises any of amino acid residues 1–27 of SEQ ID NO: 2;

A comprises amino acid residues 28–69 of SEQ ID NO: 2;

B comprises amino acid residues 70–90 of SEQ ID NO: 2;

and Y comprises any of amino acid residues 91–170 of SEQ ID NO: 2. The present invention further relates to fragments of TnI wherein the fragment has a greater immunologic reactivity than intact cTnI when the fragment and intact cTnI are reacted with a monoclonal antibody, which has an epitopic site on the fragment.

21 Claims, 19 Drawing Sheets

OTHER PUBLICATIONS

Farrah C., et al. "Structural And Regulatory Functions of the NH2– and COOH–terminal Regions of Skeletal Muscle Troponin I." The Journal of Biological Chemistry. vol. 269, No. 7, 5230–5240, 1994.

Fujita–Becker, S. et al. "Reconstitution of Rabbit Skeletal Muscle Troponin from the Recombinant Subunits All Expressed in and Purified from E. Coli." J. Biochem 114, 438–444 (1993).

Grabarek, Z. et al. "Proteolytic Fragments of Troponin C" The Journal of Biological Chem. Vo. 256 No. 24, 13121=13127, 1981.

Greaser, M. et al. "Reconstitution of Troponin Activity from Three Protein Components." The Journal of Biological Chemistry. vol. 246, No. 13, 4226–4233, 1971.

Greaser, M. et al. "Purification and properties of the Components from Troponin." The Journal of Biological Chemistry vol. 248, No. 6, 2125–2133. 1973.

Guo, X. et al. "Mutagenesis of Cardiac Troponin I." The Journal of Biological Chemistry, vol. 269, No. 21, 15210–15216, 1994.

Hastings, K.E.M., et al., J. Biol. Chem. 266(29):19659–19665, 1991.

Katus, H., et al. "Proteins of the Troponin Complex", Laboratory Medicine, vol. 23, No. 5, 1992.

Larue, C. et al., Molecular Immunology, 29(2):271–278, 1992.

Leszyk, J. et al., Biochemistry, 27:2821–2827, 1988.

Malnic, et al. "Assembly of functional skeletal muscle troponin complex in *Escherichia coli*." J. Biochem. 222, 49–54, 1994.

Morjana, N. et al., "Biochemical And Immunological Properties of a Cyanogen Bromide Fragment of Human Cardiac Troponin I.", FASEB Journal, Abstract #1706, vol. 10, No. 6 (1996).

Morjana, N. et al., "The Reversible Denaturation of Cardiac Troponin–I.", FASEB Journal Abstract #1232, vol. 9, No. 6, 1995.

Ojima, T. et al., "Amino Acid Sequence of C–Terminal 17 kDa CNBr–Fragment of Akazara Scallop Troponin–I", J. Biochem. 117, 158–162 (1995).

Ottlinger, M. et al., "Troponin T and Troponin I: New Serum Markers of Myocardial Damage." CLN, Jul. 1994.

Panteghini, M., "Cardiac Myosin Light Chains", Laboratory Medicine, vol. 23, No. 5318–322 (1992).

Potter, J.D., "Preparation of Troponin and Its Subnits[sic]", Methods in Enzymology, vol. 85: 241–263 (1982).

Potter, J.D., et al., "The Regulation of Cardiac Muscle Contraction by Troponin." Cell Motility and Muscle, vol. 2. 245–255 (ed. Dowben, R.N. & Shay, J.W.) (1982).

Reinach, F. "Cloning Expression, and Site–directed Mutagenesis of Chicken Skeletal Muscle Troponin C." Journal of Biological Chemistry. vol. 263, No. 5, 2371–2376, 1988.

Sheng. Z. et al. "Isolation, Expression, and Mutation of a Rabbit Skeletal Muscle cDNA Clone for Troponin I." The Journal of Biological Chemistry, vol. 267, No. 35, 25407–25413, 1992.

Swenson, C. et al. "Interaction of Troponin C and Troponin C Fragments with Troponin I and the Troponin I Inhibitory Peptide." Biochem. vol. 31, No. 13, 1992, 3420–3429.

Syska, H. et al., Biochem J. 153 (2) 375–387, 1976.

Trinquier, S. "Highly Specific Immunoassay for Cardiac Troponin I Assessed in Noninfarct Patients with Chronic Renal Failure or Severe Polytrauma", Clinical Chemistry, vol. 41, No. 11, 1995.

Tsuchida, K. et al. "Degradation of Myocardial Structural Proteins in Myocardial Infarcted Dogs is Reduced by Ep459, a Cysteine Proteinase Inhibitor", Biol. Chem. Hoppe–Seyler vol. 367, pp. 39–45 (1986).

Vaidya, H.C., "Myoglobin", Laboratory Medicine vol. 23, No. 5, (1992).

Vallins, W.J. et al., FEBS Letters 270(1,2):57–61, 1990.

Whipple, G. et al., "Degradation of Myofibrillar Proteins By Extractable Lysosomal Enzymes and m–Calpain, and the Effects of Zinc Chloride", J. Anim. Sci. 1991, 69:4449–4460.

Wilkinson, J.M. et al, Nature, 271:31–35, 1978.

Wu, A.H. "Creatine Kinase MM and MB Isoforms", Laboratory Medicine vol. 23, No. 5 (1992).

Wu, A.H. et al. "Cardiac Troponin–T Immunoassay for Diagnosis of Acute Myocardial Infarction." Clin. Chem. 40/6, 900–907, 1994.

Zot A. et al. "Structural Aspects of Troponin–Tropomyosin Regulation of Skeletal Muscle Contraction." Ann. Rev. Biophys. Chem. 1987. 16:1535–59.

* cited by examiner

Western Blot Analysis of MI Patient Serum (Pool)

TnI forms in Individual MI Patient Serum

N-terminal Processing of MI Patient Serum TnI

```
    1                                                    25
(H) A-D-G-S-S-D-A-A-R-E-P-R-P-A-P-A-P-I-R-R-R-S-S-N-Y-
(F)

26                                                   50
    R-A-Y-A-T-E-P-H-A-K-K-K-S-K-I-S-A-S-R-K-L-Q-L-K-T-
      A-Y-A-T-E-P-H-A-K-K-K-S-K-I-S-A-S-R-K-L-Q-L-K-T-

51
    L-L-L-Q-I-A-K-Q-E-L-E-R-E-A-E-E-R-R-G-
    L-L-L-Q-I-A-K-Q-E-L-E-R-E-A-E-E-R-R-G-
```

H: Human TnI (native)
F: Patient Serum TnI Fragment

← TnI

← TnI Fragment

Degradation of Bovine TnI and r-TnI in Human Serum
A) r-TnI in Normal Human Serum
B) Bovine TnI in Normal Human Serum
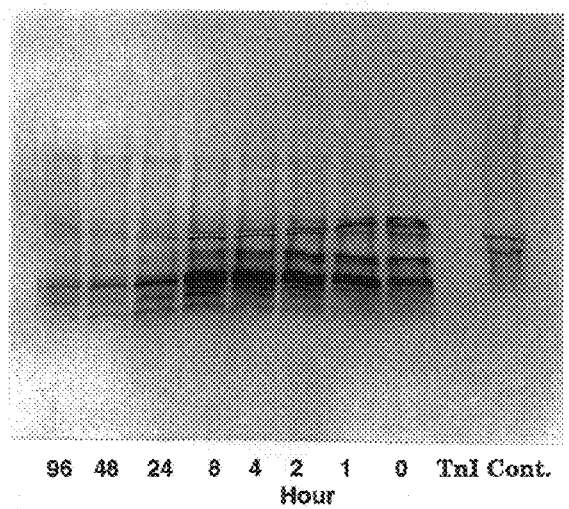
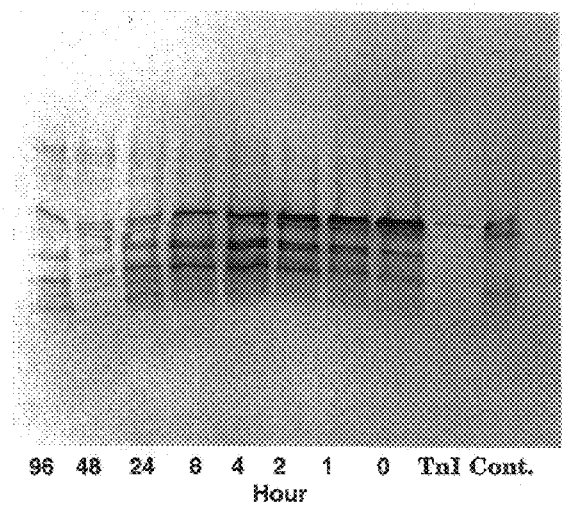
FIG. 6A
FIG. 6B

Degradation of Bovine TnI and r-TnI in MI Patient Serum Depleted of TnI

A) r-TnI in MI Patient Serum

B) Bovine TnI in MI Patient Serum 96 48 24 8 4 2 1 0 TnI Cont.
Hour 96 48 24 8 4 2 1 0 TnI Cont.
Hour

Western Blot Analysis of Human TnI Forms

- Lane #1 Molecular Weight Standard.
- Lane #2 Recombinant TnI (rTnI).
- Lane #3 CNBr TnI Isoform (TnI-153 a.a.) 1 → 153.
- Lane #4 TnI Isoform II (TnI-88 a.a.) 6 → 95.

(Ref. Human Heart CNBr TnI Isoform, Nihmat Morjana and Curtis DeMarco, patent application).

Amino Acid Sequence of TnI Forms

```
        -7            -1 0 1
(r)  M-A-S-M-T-L-W-M-A-D-G-S-S-D-A-A-R-E-P-R-P-A-P-A-P-
(h)                  A-D-G-S-S-D-A-A-R-E-P-R-P-A-P-A-P-
(I)                  A-D-G-S-S-D-A-A-R-E-P-R-P-A-P-A-P-

I-R-R-S-S-N-Y-R-A-Y-A-T-E-P-H-A-K-K-K-S-K-I-S-A-S-R-K-
I-R-R-S-S-N-Y-R-A-Y-A-T-E-P-H-A-K-K-K-S-K-I-S-A-S-R-K-
I-R-R-S-S-N-Y-R-A-Y-A-T-E-P-H-A-K-K-K-S-K-I-S-A-S-R-K-

L-Q-L-K-T-L-L-L-Q-I-A-K-Q-E-L-E-R-E-A-E-E-R-R-G-E-K-G-R-
L-Q-L-K-T-L-L-L-Q-I-A-K-Q-E-L-E-R-E-A-E-E-R-R-G-E-K-G-R-
L-Q-L-K-T-L-L-L-Q-I-A-K-Q-E-L-E-R-E-A-E-E-R-R-G-E-K-G-R-

A-L-S-T-R-C-Q-P-L-E-L-T-G-L-G-F-A-E-L-Q-D-L-C-R-Q-L-H-
A-L-S-T-R-C-Q-P-L-E-L-T-G-L-G-F-A-E-L-Q-D-L-C-R-Q-L-H-
A-L-S-T-R-C-Q-P-L-E-L-T-G-L-G-F-A-E-L-Q-D-L-C-R-Q-L-H-
           |                                 |
          cam                               cam A-R-V-D-K-V-D-E-E-R-Y-D-I-E-A-K-V-T-K-N-I-T-E-I-A-D-L-
A-R-V-D-K-V-D-E-E-R-Y-D-I-E-A-K-V-T-K-N-I-T-E-I-A-D-L-
A-R-V-D-K-V-D-E-E-R-Y-D-I-E-A-K-V-T-K-N-I-T-E-I-A-D-L-

TROPONIN I FORMS AND USE OF THE SAME

FIELD OF THE INVENTION

This invention relates to the field of the diagnosis and treatment of myocardial infarction (MI). More particularly it relates to novel fragments of cardiac Troponin I and their use.

BACKGROUND OF THE INVENTION

Rapid and simple tests that can be used to accurately diagnose the occurrence of MIs are extremely important. One biochemical test that can be used in the diagnosis of MI is the MB isoenzyme of creatine kinase ("CK-MB"). However, CK-MB can also be found in skeletal muscle and in blood after skeletal muscle injury. Thus, CK-MB is not completely specific for cardiac muscle. See, e.g., Cummins, et al. (1987), "Cardiac-Specific Troponin I Radioimmunoassay in the Diagnosis of Acute Myocardial Infarction", *American Heart Journal*, Jun. 1987, Vol. 113, No. 6. Another disadvantage of the CK-MB test is that the amount of CK-MB in the skeletal muscle varies with the degree of skeletal muscle regeneration, information which may often not be known when administering a test or analyzing a test result for MI. Another disadvantage of the CK-MB test is that CK-MB remains elevated for only 2–3 days after the onset of chest pain. For patients admitted after that time, the CK-MB test will be of limited, if any, value. See, e.g., Cummins, et al. (1987). Thus, due to the lack of specificity of the CK-MB test, and the limited time frame for its use as a diagnostic tool, CK-MB is not the MI test of choice.

Other enzyme assays exist, such as lactate dehydrogenase (LDH) and glutamic oxaloacetic transaminase (GOT). However, the frequent serial measurements required in the very early hours after the onset of chest pain can present difficulties for an absolute specific diagnosis. See, e.g., Larue, et al. (1992), "New Monoclonal Antibodies as Probes for Human Cardiac Troponin I: Epitopic Analysis With Synthetic Peptides", *Molecular Immunology*, Vol. 29, No. 2, pp. 271–278. Thus, the prior art has recognized the need for an accurate cardiac-specific biological parameter detectable in serum very soon after MI and remaining present for more than 2–3 days after the onset of MI.

Troponin I (TnI) is the inhibitory sub-unit of Troponin, a thin filament regulatory protein complex, which confers calcium sensitivity to the cardiac and striated muscle. The Troponin complex consists of three subunits: Troponin T (TnT), the tropomyosin binding subunit, Troponin C (TnC), the Ca++ binding subunit; and TnI, which inhibits the actomyosin Mg++ ATPase.

Troponin I exists in three isoforms: two skeletal muscle isoforms (fast and slow) (Molecular Weight=19,800 daltons) and a cardiac TnI isoform (cTnI) with an additional 31 residues (human TnI) on the N-terminus resulting in a molecular weight of 23,000 daltons. Cardiac TnI is uniquely located in the myocardium where it is the only isotype (Cummins, P. and Perry, V. S., (1978) *Biochem. J.* 171:251–259. The amino acid sequence of cardiac TnI from various species has been determined. There is little difference in the primary structure between human cardiac TnI (209 amino acids) and bovine cardiac TnI (211 amino acids). More differences are seen between cardiac TnI and skeletal muscle TnI. (Leszky et al. (1988) *Biochemistry*, Vol. 27, pp. 2821–2827).

Cardiac TnI (cTnI) rapidly appears in human serum (within approximately 4 to 6 hours) following a MI. It reaches a peak level after 18–24 hours and remains at elevated levels in the blood stream for up to 6 to 7 days. Thus, immunoassays which can test for human cTnI are valuable to the medical community and to the public.

The TnI released into circulation is very specific for myocardial injury. Little information is presently known about Troponin I present in the circulation after being released from the heart. Knowledge about TnI in MI patient serum is very important for studying the effects of MI on heart muscle as well as for developing assays to assist in the diagnosis and treatment of MI patients.

It is desirable to use an immunologically reactive human cTnI form comparable to that detected in MI patient serum. We found that MI patient serum contains TnI fragment(s) which is the result of the C-terminal processing of cTnI molecule. The high sequence homology found in the C-terminal region between cardiac TnI and skeletal muscle TnI (Larue et al. (1992); Vallins et al. (1990) *FEBS Lett*. Vol. 270, pp. 57–61; Leszky et al. (1988)) produce TnI antibodies directed against this region having non-cardiac specificity. (Larue et al. (1992)). Our data and Larue et al. 1992 suggest that most of the known cTnI specific antibodies have their epitopes located approximately in the first 75% of the TnI molecule. Therefore, this portion of the TnI molecule should function as a MI specific cTnI isoform in most immunoassay systems. Consequently, MI assays that look at cTnI have become important.

However, present TnI immunoassays use different TnI antigens in the calibrators and the controls. For example, Dade International Inc. (hereinafter sometimes referred to as "Dade") presently sells a cTnI Immunoassay Kit in Europe and U.S.A. using a synthetic peptide in the calibrators and in the controls. This product is the STRATUS® Cardiac Troponin-I assay, a radial partition immunoassay. It would be advantageous to use a native human TnI form in the calibrators and controls in order to more accurately simulate the conditions in patient serum.

The use of the native human peptide is not practical because native human cTnI form is difficult to obtain due to the scarcity of human heart muscle. Moreover, native human cTnI is highly subject to proteolytic degradation during purification. The availability of human recombinant TnI ("r-TnI") can facilitate the production of this cTnI form. The r-TnI, unlike the native human cTnI, can be produced and purified in acceptable quantities. As expressed by Dade, the primary structure of r-TnI contains 226 amino acids (SEQ ID NO: 1); 209 of them represent the TnI sequence (SEQ ID NO: 2). In addition to the primary sequence of cTnI (SEQ ID NO: 2), r-TnI has a leading sequence of 8 amino acids (MASMTLWM) on the N-terminal, and a tail sequence of 9 amino acids (PMVHHHHHH) on the C-terminal (SEQ ID NO: 1). The primary structure of the r-TnI molecule has methionine residues at positions −7, −4, 0, 153, 154, 200 and 211 (SEQ ID NO: 1).

U.S. application Ser. No. 08/564,526 discloses a human cTnI fragment generated from human r-TnI by chemical cleavage. The cleavage of r-TnI by cyanogen bromide (CNBr) results in a major polypeptide of 153 amino acids, hereinafter referred to as the "CNBr-cTnI isoform" (SEQ ID NO: 3). The CNBr-cTnI isoform represents 73% of the primary structure of human cTnI and is immunologically more reactive than r-TnI. The purified CNBr-cTnI isoform has an average of 3–4 times more reactivity than r-TnI and lower non-specific binding, as measured by radial partition immunoassay. The molecular size of the CNBr-cTnI isoform is comparable in molecular weight to a major degradation product of native cardiac TnI in MI patient serum. The CNBr-cTnI isoform can be used as calibrators or controls in various cTnI immunoassays. The CNBr-cTnI isoform has increased stability over the synthetic peptide currently used in the Dade TnI immunoassay.

Identifying stable and active cTnI forms that can be used as calibrators, controls or in other areas would be very important. Even though the 153 amino acid CNBr-isoform of r-TnI has a greater immunoreactivity than r-TnI and is more stable that the synthetic peptide currently used, there are advantages to using the native TnI as it exists in MI patient serum. For example, as mentioned above, the use of native cTnI in controls and calibrators in assays to test for cTnI would more accurately simulate the conditions in the test sample, leading to more accurate assay results.

Furthermore, while the assays presently used to detect cTnI in MI patient serum are sandwich assays, other types of assays are possible. For example, competitive assays can be used to detect cTnI. It would be useful to use an immunologically reactive human cardiac TnI form comparable to that in MI patient serum in a competitive-type assay for cTnI.

SUMMARY OF THE INVENTION

The present invention relates to cardiac Troponin I fragments. More specifically, the invention relates to an isolated fragment of human cardiac TnI comprising the following sequence

X-A-B-Y wherein

X comprises any of amino acid residues 1–27 of SEQ ID NO: 2;

A comprises amino acid residues 28–69 of SEQ ID NO: 2;

B comprises amino acid residues 70–90 of SEQ ID NO: 2; and Y comprises any of amino acid residues 91–170 of SEQ ID NO: 2.

In one preferred embodiment of the present invention, X is a fragment comprising any or all of the residues 1–27 of SEQ ID NO:2 and any and all fragments thereof which include residue number 27 and any consecutive residues up to and including residue 2 of SEQ ID NO:2. In other preferred embodiments of the present invention, X comprises amino acid residues 1–27, 2–27, 4–27, 6–27, 10–27, 15–27, 20–27, 25–27, and 27 of SEQ ID NO: 2. In other preferred embodiments, X comprises residues 1–27, 2–27, 3–27, 4–27, 5–27, 6–27, 7–27, 8–27, 9–27, 10–27, 15–27, 20–27, 21–27, 22–27, 23–27, 24–27, 25–27, 26–27, and 27 of SEQ ID NO: 2.

In one preferred embodiment of the present invention, Y comprises any or all of amino acid residues 91–170 of SEQ ID NO:2 and any and all fragments thereof which include residue 91 and any consecutive residues up to and including residue 170. In certain preferred fragments, Y comprises any of residues 91–92, 91–93, 91–94, 91–95, 91–96, 91–97, 91–98, 91–99, 91–100, 91–105, 91–110, 91–115, 91–116, 91–117, 91–118, 91–119, 91–120, 91–121, 91–122, 91–123, 91–124, 91–125, 91–126, 91–127, 91–128, 91–129, 91–130, 91–131, 91–132, 91–133, 91–134, 91–135, 91–136, 91–137, 91–138, 91–139, 91–140, 91–141, 91–142, 91–143, 91–144, 91–145, 91–146, 91–147, 91–148, 91–149, 91–150, 91–151, 91–152, 91–153, 91–154, 91–155, 91–160, 91–165, or 91–170 of SEQ ID NO: 2. More preferably, Y comprises any of residues 91–95, 91–100, 91–105, 91–110, 91–115, 91–120, 91–130, 91–140, 91–145, 91–150, 91–153, 91–155, 91–160, 91–165, and 91–170 of SEQ ID NO 2.

In other preferred embodiments, X comprises residues 1–27, 6–27, or 27 of SEQ ID NO: 2 and Y comprises any of residues 91–95, 91–120, 91–121, 91–122, 91–123, 91–124, 91–125, 91–126, 91–127, 91–128, 91–129, 91–130, 91–131, 91–132, 91–133, 91–134, 91–135, 91–136, 91–137, 91–138, 91–139, 91–140, 91–141, 91–142, 91–143, 91–144, 91–145, or 91–153 of SEQ ID NO: 2.

Still other preferred embodiments of the present invention, X comprises residues 1–27 and Y comprises any of 91–135, 91–136, 91–137, 91–138, 91–139, 91–140, 91–141, 91–142, 91–143, 91–144, 91–145, or 91–153 of SEQ ID NO: 2.

The present invention further relates to fragments of TnI wherein the fragment has a greater immunologic reactivity than intact cTnI when the fragment and intact cTnI are reacted with a monoclonal antibody, which has an epitopic site on the fragment. Preferably the immunologic reactivity has at least about two times, more preferably about two to four times, the reactivity of intact cTnI when measured by STRATUS® cTnI Immunoassay, or any radial partition immunoassay.

The present invention further relates to fragments of TnI wherein the fragment has an apparent molecular weight of about 18,000. The present invention further relates to fragments of TnI wherein the fragment has an apparent molecular weight of about 14,000.

The present invention further relates to fragments of TnI wherein the fragment comprises the binding site for TnC.

The present invention further relates to methods of isolating from blood or serum a cTnI fragment of native cardiac Troponin I.

The methods of the present invention for isolating fragments of native cTnI in blood or serum samples comprise: immobilizing antibodies to cTnI on a substrate; mixing the sample to be tested with the antibody-coated substrate; incubating the mixture for an appropriate length of time to obtain antibody-bound TnI; removing the antibody-bound TnI from the mixture and eluting the TnI from the antibody-coated substrate. The method of the present invention further comprises measuring the amount of TnI in the final eluant.

The present invention further relates to a method of isolating from blood or serum a fragment of human cardiac TnI comprising the sequence X-A-B-Y, where X, A, B and Y are as defined above, the method comprising extracting the cTnI fragment using latex beads coated with anti-TnI monoclonal antibodies.

The present invention also relates to a fragment of human cardiac TnI isolated from blood or serum samples by the method comprising: immobilizing antibodies to cTnI on a substrate; mixing the sample to be tested with the antibody-coated substrate; incubating the mixture for a length of time; removing the antibody-bound TnI from solution; and, eluting the TnI from the antibody-coated substrate.

The present invention further relates to methods of isolating a troponin complex of TnI, TnC and TnT subunits comprising: immobilizing antibodies to at least one subunit on a substrate; mixing the sample to be tested with the antibody-coated substrate; incubating the mixture for a predetermined length of time; removing the antibody-bound complex from solution; and, eluting the complex from the antibody-coated substrate.

The present invention further relates to the use of cardiac Troponin I fragments. One use of such a fragment is as a calibrator for a TnI immunoassay comprising: a) a known amount of the fragment of human cardiac TnI comprising the sequence X-A-B-Y, where X, A, B and Y are as defined above; and b) serum or calibrator base. In certain embodiments, the calibrator base comprises a buffer containing BSA.

The present invention further provides a control for a TnI immunoassay comprising: a) a known amount of the fragment of human cardiac TnI comprising the sequence X-A-B-Y, where X, A, B and Y are as defined above; and b) serum or control base. In certain embodiments, the control base comprises a buffer containing BSA.

DETAILED DESCRIPTION OF THE DRAWINGS

FIG. 6a shows degradation of human r-TnI in normal human serum.

FIG. 6b shows degradation of bovine TnI in normal human serum.

FIG. 13 depicts the alignment of the human cardiac Troponin I amino acid sequences.

DETAILED DESCRIPTION OF THE INVENTION

Figure 1:
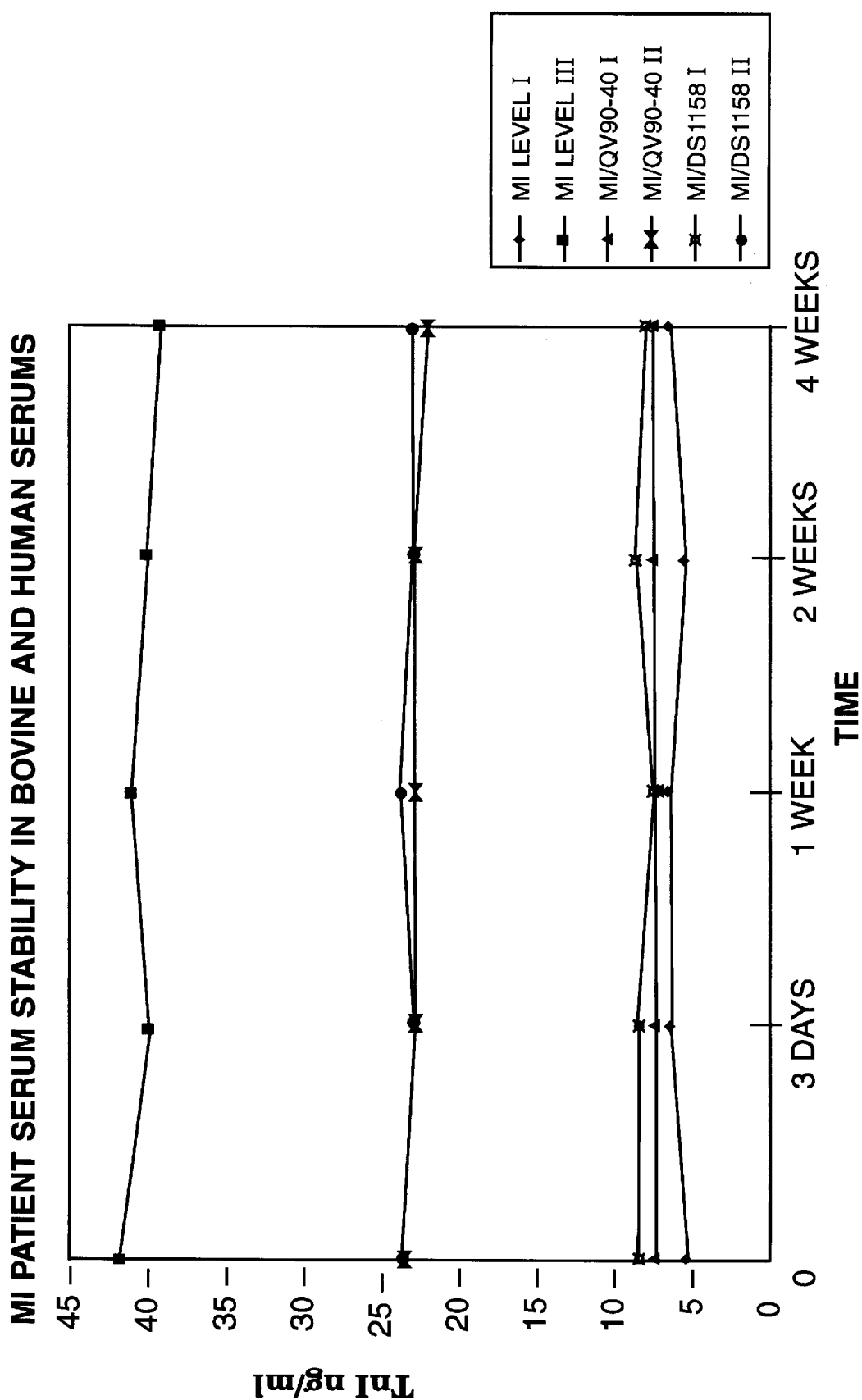
FIG. 1 is a graph showing stability of MI patient serum TnI.

While cTnI levels in MI patient serum are very stable, purified TnI, in serum is degraded. For example, FIG. 1 shows that cTnI levels in MI patient serum are maintained for up to 4 weeks when the serum is stored at 4° C. (TnI activity of MI patient serum (■, ♦), in bovine serum (Δ, X) and in normal human serum (*, ●)). The mixtures were incubated at 4° C. and the TnI recovery was measured using STRATUS® II TnI Immunoassay (Dade International Inc.). However, cTnI purified from patient serum loses its activity rapidly after spiking into MI patient serum, under the same conditions (not shown). The solid stability of TnI recovered from patient serum cannot be reproduced in vitro using the purified TnI subunit.

We have found that cleavage fragments of TnI will be active, yet are substantially more stable than intact cTnI. Using the methods of the present invention, further described below, major TnI fragments were isolated from MI patient serum pools using immobilized anti-TnI antibodies which recognize various epitopic sites on the TnI molecule. Two fragments of the present invention have apparent molecular weights of about 18,000 KD and about 14,000 KD respectively (hereinafter referred to as "18,000 fragment" and "14,000 fragment" respectively).

The TnI fragments are generated as a result of sequential processing from the C-terminal of TnI. Such processing produces the 18,000 fragment followed by the 14,000 fragment. Both TnI fragments, or either one alone, are present in serum of MI patients (See FIG. 4 and Example IV below). The presence of either one or two bands indicates that the two bands are generated by sequential processing of the TnI molecule. Partial processing from the N-terminal of TnI is also seen and occurs with the generation of the smaller fragment. FIG. 5 shows a schematic representation for processing of MI patient serum TnI. Very little intact TnI is detected in patient serum after MI.

Intact human cTnI is known to have the following sequence:
A-D-G-S-S-D-A-A-R-E-P-R-P-A-P-A-P-I-R-R-S-S-N-Y-R-A—Y-A-T-E-P-H-A-K-K-K-S-K-I-S-A-S-R-K-L-Q-L-K-T-L-L-L-Q—I-A-K-Q-E-L-E-R-E-A-E-E-R-R-G-E-K-G-R-A-L-S-T-R-C-Q-P—L-E-L-T-G-L-G-F-A-E-L-Q-D-L-C-R-Q-L-H-A-R-V-D-K-V-D-E—E-R-Y-D-I-E-A-K-V-T-K-N-I-T-E-I-A-D-L-T-Q-K-I-F-D-L-R—G-K-F-K-R-P-T-L-R-R-V-R-I-S-A-D-A-M-M-Q-A-L-L-G-A-R-A—K-E-S-L-D-L-R-A-H-L-K-Q-V-K-K-E-D-T-E-K-E-N-R-E-V-G-D—W-R-K-N-I-D-A-L-S-G-M-E-G-R-K-K-K-F-E-S (SEQ ID NO: 2). (Armour, K. L. et al (1993) "Cloning and Expression in *Escheria Coli* of the cDNA Encoding Human Cardiac Tropinin I," *Gene*, 131(2):287–92).

We have now discovered a series of TnI fragments. These fragments are typically active and more stable in serum than full length TnI. The fragments of the present invention comprise a peptide X-A-B-Y wherein X, A, B and Y are defined below. X comprises any of amino acid residues 1–27 of SEQ ID NO: 2. Preferred residues for X include residues 1–27, 2–27, 3–27, 4–27, 5–27, 6–27, 7–27, 8–27, 9–27, 10–27, 15–27, 20–27, 21–27, 22–27, 23–27, 24–27, 25–27, 26–27, and 27 of SEQ ID NO: 2. More preferably, X can be any of amino acid residues 1–27, 2–27, 4–27, 6–27, 10–27, 15–27, 20–27, 25–27, and 27 of SEQ ID NO: 2.

A comprises amino acid residues 28–69 of SEQ ID NO: 2. B comprises amino acid residues 70–90 of SEQ ID NO: 2. Y comprises any of amino residues 91–170 of SEQ ID NO: 2. Preferred residues of Y include residues 91–92, 91–93, 91–94, 91–95, 91–96, 91–97, 91–98, 91–99, 91–100, 91–105, 91–110, 91–115, 91–116, 91–117, 91–118, 91–119, 91–120, 91–121, 91–122, 91–123, 91–124, 91–125, 91–126, 91–127, 91–128, 91–129, 91–130, 91–131, 91–132, 91–133, 91–134, 91–135, 91–136, 91–137, 91–138, 91–139, 91–140, 91–141, 91–142, 91–143, 91–144, 91–145, 91–146, 91–147, 91–148, 91–149, 91–150, 91–151, 91–152, 91–153, 91–154, 91–155, 91–160, 91–165, 91–170 of SEQ ID NO: 2. More preferably, Y can be any of 91–95, 91–100, 91–105, 91–110, 91–115, 91–120, 91–130, 91–140, 91–145, 91–150, 91–153, 91–155, 91–160, 91–165, 91–170 of SEQ ID NO: 2.

In certain preferred embodiments of the present invention, X comprises residues 1–27, 6–27, or 27 of SEQ ID NO: 2, while Y comprises any of residues 91–95, 91–120, 91–121, 91–122, 91–123, 91–124, 91–125, 91–126, 91–127, 91–128, 91–129, 91–130, 91–131, 91–132, 91–133, 91–134, 91–135, 91–136, 91–137, 91–138, 91–139, 91–140, 91–141, 91–142, 91–143, 91–144, 91–145, or 91–153 of SEQ ID NO: 2.

In other preferred embodiments, X comprises residues 1–27 and Y comprises any of 91–135, 91–136, 91–137, 91–138, 91–139, 91–140, 91–141, 91–142, 91–143, 91–144, 91–145, or 91–153 of SEQ ID NO: 2.

In still other preferred embodiments, X comprises residue 27 and Y comprises any of 91–120, 91–121, 91–122, 91–123, 91–124, 91–125, 91–126, 91–127, 91–128, 91–129, or 91–130. In one embodiment, X comprises residues 6–27 and Y comprises 91–95 of SEQ ID NO: 2.

Figures 4A, 4B:
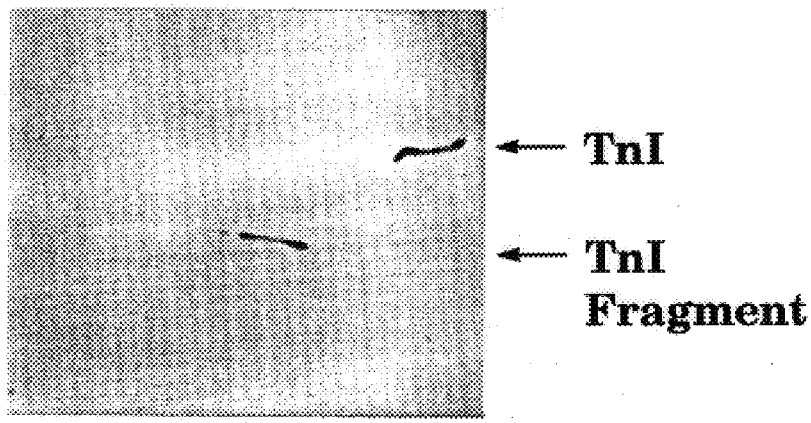
FIG. 4a shows alignment of the N-terminal sequence of patient serum TnI fragment with the N-terminal of human cardiac TnI.
FIG. 4b shows the lower molecular weight TnI fragment, isolated from MI patient serum and Western blotted.
Figure 5:
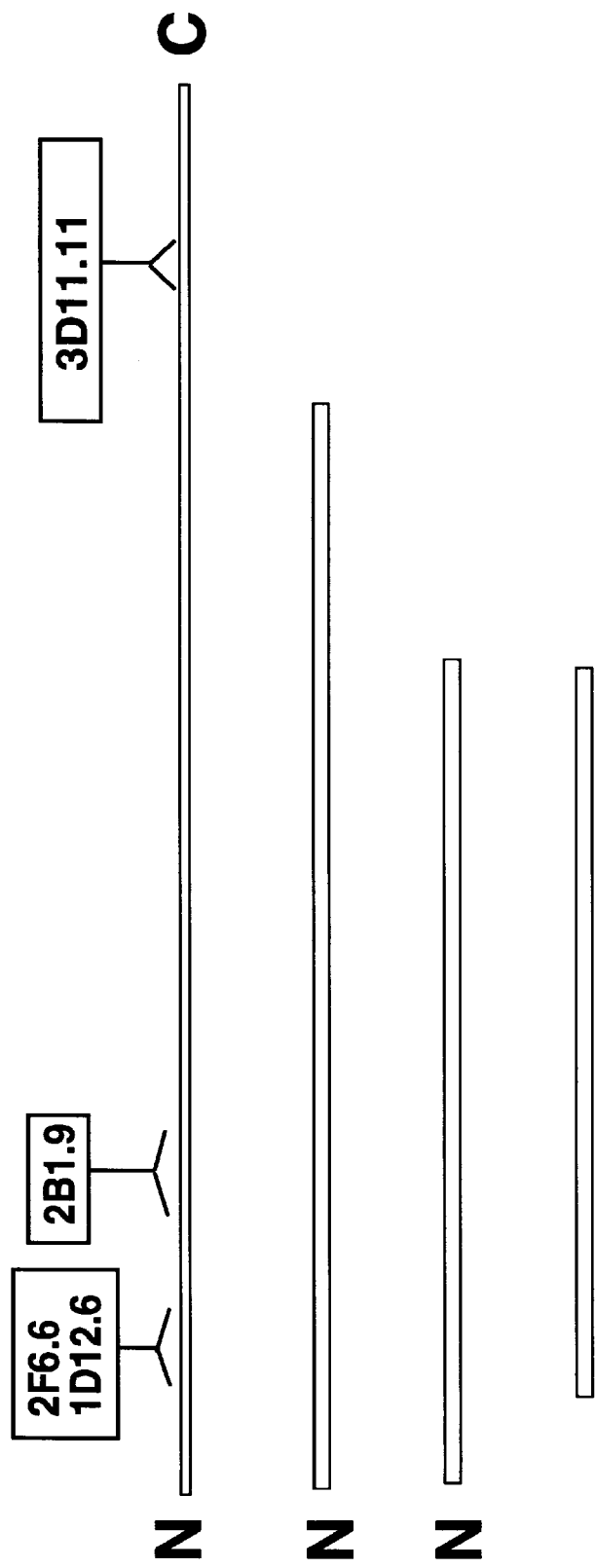
FIG. 5 shows Troponin I processing after MI.

The lower molecular weight 14,000 TnI fragment, isolated from a pool of patient serum and sequenced for N-terminal identification, shows alignment of the N-terminal of TnI fragment with intact human TnI (FIG. 4a). The N-terminal sequence of the TnI 14,000 fragment starts at about position 27 (Ala) in intact human cardiac TnI. The 14,000 fragment is approximately 100 amino acids long, ending in the region from about amino acid 120 to about amino acid 130 in intact cTnI. The N-terminal sequence of the 18,000 fragment starts at or very near the N-terminus of the intact human cTnI. The 18,000 fragment is approximately 140 amino acids long, ending in the region from about amino acid number 135 to about 145 in intact cTnI. Thus, one preferred group of fragments has X as 25–27, 26–27 or 27 of SEQ ID NO:2 and Y as 91 to any of 135–145 of SEQ ID NO:2.

Fragments of native cTnI in blood or serum samples can be isolated by using antibodies to cTnI which are immobilized on a substrate resulting in an antibody-coated substrate; adding the sample to be tested to the antibody-coated substrate; incubating the mixture for an appropriate length of time; removing the antibody-bound TnI from solution and eluting the TnI from the antibody-coated substrate. This method preferably further comprises measuring the amount of TnI in the final eluant.

The TnI antibodies are immobilized on the substrate by methods known in the art, e.g., physical adsorption or covalent attachment. The time required for maximum attachment of the TnI antibodies to the substrate can readily be determined empirically based upon the present disclosure. Preferably, the incubation time is between about ½ hour to about 12 hours, more preferably from about ½ hour to about 3 hours. Most preferably, the incubation time is from about 1 hour to about 2 hours.

Any solid phase known in the art can be used as a substrate in the present methods, but the following substrates are preferred: beads, microtitre plates, different resins. Preferably, the substrate is one that enables small scale assays to be run. Therefore, in certain preferred embodiments the substrate comprises beads, e.g., latex beads, beads made of polystyrene and styrene derivatives.

Any antibody which specifically binds the TnI fragments can be immobilized for use in isolating the cTnI fragments according to the methods of the present invention as determined by one of ordinary skill in the art. That is, the fragment must contain the binding sites for the antibody (Bodor, et al., 1992)(incorporated herein by reference). Preferably, the antibody also allows dissociation of the isolated fragments under the appropriate conditions for purification.

Table 1 shows antibody specificity to human cTnI of selected antibodies (from Bodor, et al., 1992).

TABLE 1

SUMMARY OF ANTIBODY SPECIFICITY

| Antibody sTnI | Antigen | | | |
|---|---|---|---|---|
| | Human cTnI | Human sTnI | Canine cTnI | Canine sTnI |
| 2B1.9 | + | – | + | – |
| 5D4.1 | +[a] | +[a] | +[a] | +[a] |
| 3C5.10 | + | + | + | + |
| 1E11.3 | + | – | + | – |
| 7B11.4 | + | + | + | + |
| 3D11.11 | + | – | + | – |
| 1D12.6 | + | – | + | – |
| 2F6.6 | + | – | + | – |

+, $A_{405\ nm} \geq 0.400$; –, $A_{405\ nm} < 0.125$.
[a]Reacts only when TnC is present.

Because MI patient serum TnI appears to be processed primarily from the C-terminal end, it is preferable that the antibodies used have epitopes which are not near the C-terminal end of cTnI (e.g., 2F6.6, 2B1.9 and 1D12.6). Preferably, the epitopes are in the N-terminal region of cTnI, subsequent to the first 28 amino acids of the native cTnI or the central section of TnI, more preferably between about 26–130 of SEQ ID NO: 2.

Various antibodies, other than anti-human cardiac TnI antibodies, can be immobilized and used for extraction of TnI provided the TnI fragments contain the appropriate epitope and specifically bind human TnI. Because of the homology between human cTnI and cardiac TnI from other mammals, antibodies raised against bovine cardiac TnI or rabbit cardiac TnI can be used for extraction. Useful antibodies can be readily determined by one of ordinary skill in the art based upon the teachings contained herein.

The antibodies 1D12.6, 2B1.9 and 2F6.6 have their epitopes at the N-terminal region of the TnI molecule, whereas the epitope for the antibody 3D 11.11 is located in the C-terminal region of cTnI. The preferred antibodies for isolating the fragments comprise 1D12.6, 2B1.9 and 2F6.6. More preferably, the antibody comprises 2B1.9. However, as discussed above, appropriate antibodies for use in the methods of the present invention can be readily determined by one of ordinary skill in the art in light of the teachings herein.

Antibodies adsorb to the substrate over a wide range of pHs, depending on the antibody and substrate chosen as well as the buffer system. Any buffer system can be used for coating the beads, provided the buffer does not interfere with the adsorption process. The appropriate buffer can be readily chosen according to methods known in the art. Although any pH is useful, a neutral pH or slightly acidic pH is preferred in certain embodiments.

The sample to be tested is combined with the antibody-coated substrate and incubated for an appropriate length of time. In embodiments in which beads are used as the substrate, the antibody-coated beads are preferably added to the sample directly. Thus, no additional buffer or additional dilutions are necessary. When the substrate is a microtitre plate, or other similar solid phase, the method of isolation of the present invention comprises adding the sample to the antibodies bound thereon, e.g., in the wells of a microtitre plate.

The TnI in the sample binds to antibody-coated substrate, e.g., beads, preferably within a few minutes. The appropriate incubation time and temperature to maximize binding can be determined by one of ordinary skill in the art based upon the teachings contained herein. In certain embodiments of the invention the incubation occurs at a temperature of from about 20° to 30° and from about 10 minutes to about 2 hours. In preferred embodiments the incubation occurs at room temperature for about 15 to 30 minutes. After the sample is incubated with the antibody-coated substrate, the TnI bound to the antibody coated substrate is recovered. Recovery comprises washing the TnI-antibody-bound substrate in an appropriate elution buffer. To obtain the TnI fragments, the elution buffer is a denaturing buffer, e.g., a buffer containing SDS. In a preferred embodiment of the present invention, the TnI-bound beads are incubated in electrophoresis sample buffer containing SDS to release the TnI fragments.

In preferred methods where the sample size is small, the recovered TnI is separated from the substrate by centrifugation. Alternatively, separation can be achieved passively, by allowing the beads to settle out, which generally occurs within a few minutes.

The methods of the present invention extract from about 70 to about 98% of TnI from MI patient serum, depending on the conditions chosen, e.g., antibody used. For example, when the TnI antibody 2B1.9 is bound to latex beads and used in the methods of the present invention, up to 98% of the TnI fragments is extracted from the sample.

The fragments of cTnI of the present invention are expected to have increased immunologic activity as compared with intact cTnI. It is believed, based on the studies with recombinant fragments of TnI as described below in Example VIII and Table 1, that the cTnI fragments of the present invention will have at least from about two to about four times the immunologic activity of intact TnI as measured by radial partition immunoassay. The fragments of recombinant TnI (rTnI) tested in Example VIII demonstrate greater reactivity using the STRATUS® Cardiac Troponin-I assay than intact rTnI. For example, a TnI fragment having 153 amino acids (from amino acid 1–153 of SEQ ID NO:2) ("TnI153") has more than about 6 times the activity of the full length recombinant cTnI ("rTnI"). A TnI fragment having 88 amino acids (from amino acid 6–95 of SEQ ID NO:2) ("TnI88") has more than about 13 times the activity of the full length recombinant cTnI.

We have found that the majority of native cTnI in human serum after a MI is associated with TnC and TnT. The presence of TnI in a complex ("Tn complex") with other troponin subunits in MI patient serum increases its stability and protects it from further degradation. In addition, the Tn complex protects the sites where cardiac-specific antibodies bind.

The Tn complex is isolated from MI patient serum according to methods of the present invention. A preferred method of isolating the Tn complex comprises incubating the sample to be tested with a substrate coated with antibodies to the subunits of the Tn complex. As stated above, many antibodies are useful, and can be selected by one of skill in the art. Examples of such antibodies include anti-TnI, anti-TnC, and anti-TnT antibodies. A preferred antibody is anti-TnI antibody. The substrate preferably comprises beads, and more preferably the substrate comprises latex beads. The bound TnI complex is eluted under conditions that do not affect association of Tn subunits, e.g. using urea. These conditions can be determined by one of skill in the art. A preferred buffer system comprises urea and lacks SDS.

The TnI fragments and Tn complex isolated according to the methods of the present invention can be used in diagnosis and treatment of MI. One exemplary use is the use of the TnI fragments or complex in calibrators and controls used in assays to detect the occurrence of MI. The calibrators are used to establish the standard curve for the assay and to calibrate the equipment used to measure the final concentration of TnI recovered. The controls are used to monitor the instrument used and test its accuracy, after it is calibrated. The amount and/or methods of the fragment used in each calibrator or control as well as the buffer components can readily be determined by one of skill in the art according to the teaching herein and based upon the type of instrumentation used.

Preferably, the buffers used for the calibrators or controls contain bovine serum albumin (BSA). In certain embodiments the buffer contains, BSA, sugars, salt and an antibacterial agent. Examples of useful buffers include HEPS, MES or TRIS buffers. A preferred buffer comprises MES buffer containing 6.5% BSA, at pH 6–7. Other preferred buffers contain a reducing agent, stabilizing protein, chelating agent and a salt as described in the copending application U.S. Ser. No. 08/400,158, incorporated herein by reference.

Alternatively, instead of a buffer, the fragments are spiked into serum, e.g., human or bovine, or into diluted serum, e.g., serum diluted 1:1 with MES buffer containing BSA.

Currently used assays for detecting cTnI in MI patient serum utilize a sandwich assay. However, the isolated cTnI fragments of the present invention can also be used to design competitive-type assays for the detection of cTnI in serum. In such an assay, a subsaturating amount of antibody to cTnI is bound to a solid phase, e.g., a microtitre plate or latex beads. The isolated native human cTnI fragment is labeled, e.g., with alkaline phosphatase, or horseradish peroxidase. A constant amount of the labeled fragment is mixed with the sample of MI patient serum containing an unknown amount of cTnI. The test sample is then allowed to bind to the subsaturating amount of cTnI antibody bound to a solid phase. The cTnI in the sample will compete with the labeled cTnI fragment for binding with the antibody-coated solid phase. Unbound proteins are removed by washing and the amount of labeled cTnI fragment bound to the solid phase is measured. The amount of labeled fragment bound to the antibody on the solid phase indicates the amount of cTnI present in the serum. If the serum contains a high concentration of cTnI, it will compete effectively with the labeled cTnI fragment and little or none of the labeled cTnI fragment will bind the antibody-coated solid phase.

The isolated TnI fragments are also useful in purifying antibodies to TnI. The isolated fragments are coupled to a matrix, e.g. sepharose, and used in an affinity column for purification.

In another diagnostic use, the TnI fragments are coupled to a solid phase and used for enzyme-linked immunosorbent assay (ELISA) testing. Solid phases for use in such a test comprises particulate material, e.g., cellulose, polyacrylamide and agarose, as well as polystyrene, polyvinyl, polycarbonate and nylon materials.

The following examples are provided to more clearly illustrate the aspects of the invention and are not intended to limit the scope of the invention.

EXAMPLES

Unless otherwise indicated, the following procedures were followed for all examples.

Bovine TnI was purified from cardiac muscle using a TnC column (Syska et al. 1974). Recombinant TnI was expressed in *E. coli* by Dade Biology Skills Center.

Figure 18:
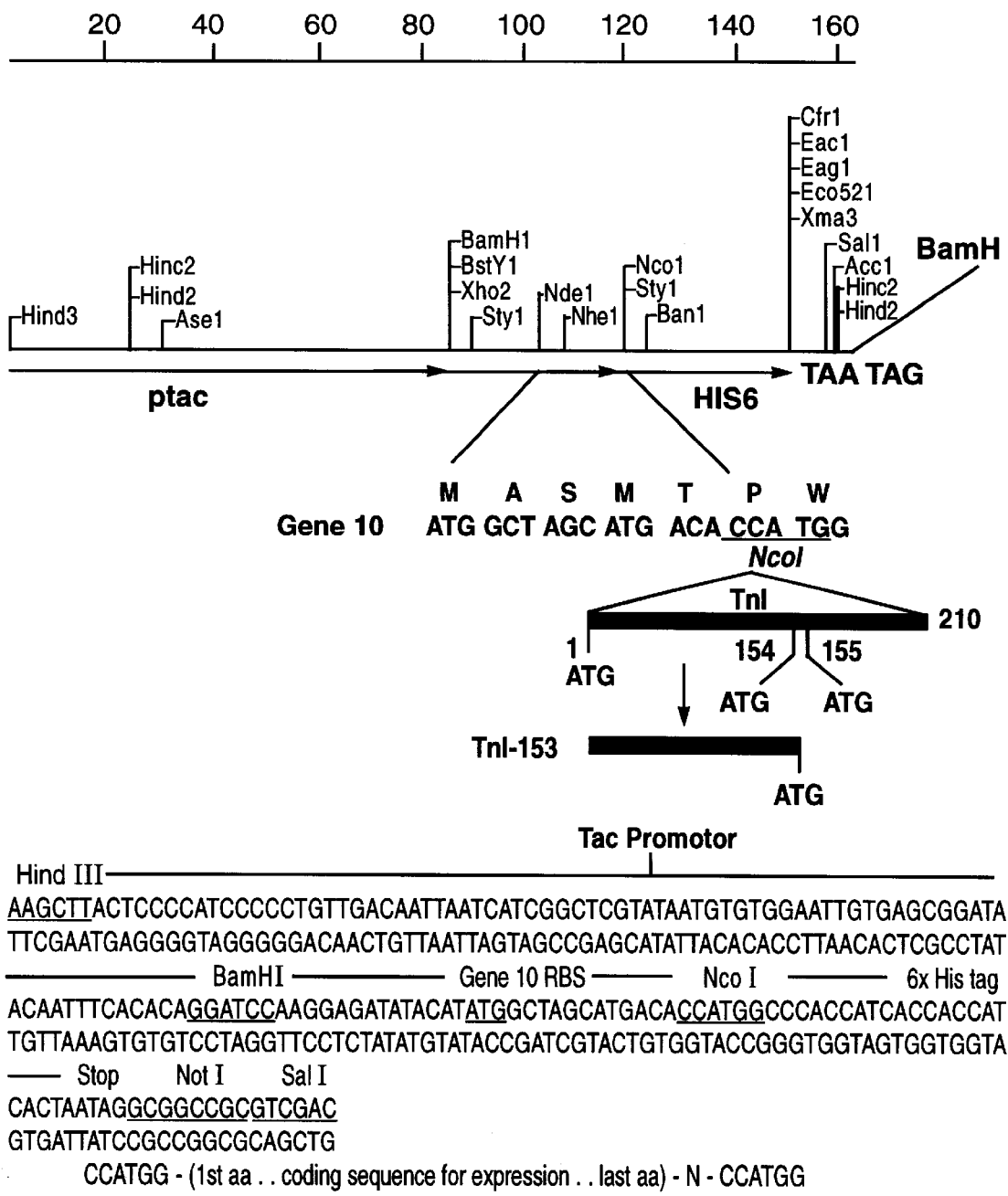
FIG. 18 shows a Map of expression vector pTac/Gene 10/Troponin I/6xHis.

The recombinant human cTnI was expressed in *E. coli* by the Dade Biology Skills Center (and we thank the Dade Biology Skills Center for providing it). TnI was cloned from human heart cDNA, which is commercially available through companies such as Strategene, by polymerase chain reaction (PCR) and was subcloned into the NcoI restriction site in the Dade constructed vector pTac 102-2, as shown in FIG. 18. (Purified TnI from bovine or human heart is also commercially available.) The vector pTac 102-2 was constructed by conventional means (see Vallins et al, (1990) Molecular Cloning of Human Cardiac Troponin I using PCR, *FEBS Lett*. 270, 57–61) to include a Hindil-Bam HI fragment containing $p^{tac}$, a strong hybrid promoter driving gene transcription. The promoter was induced in *E. coli* through IPTG, a method and technique well known to those skilled in the art. The next downstream DNA sequence is an efficient ribosomal binding site (RBS) and the N-terminal five amino acids of gene 10 for translation initiation, followed by the cloning cite NcoI. The Dade designed TnI (amino acids 1–210 (SEQ ID NO: 4), including the initiating methionine) was inserted into NcoI in frame with the N-terminus, and with six Histidine codons at the C-terminus (H156). The expressed protein contained 226 amino acids. The HIS6 C-terminus facilitated a single step purification.

Cleavage of the r-TnI molecule at the methionine residues at positions −4, 0, 153, 154, 200 and 211 by CNBr produced a major polypeptide of 153 amino acids. (SEQ ID NO: 3) The resulting polypeptide had 73% of the human cTnI primary structure (209 amino acids) (SEQ ID NO: 3), and retained the epitopes for the antibodies used in the Stratus® II TnI Immunoassay System. (See Vallins et al, (1990) *FEBS Lett*. 270, 57–61.)

Figure 14:
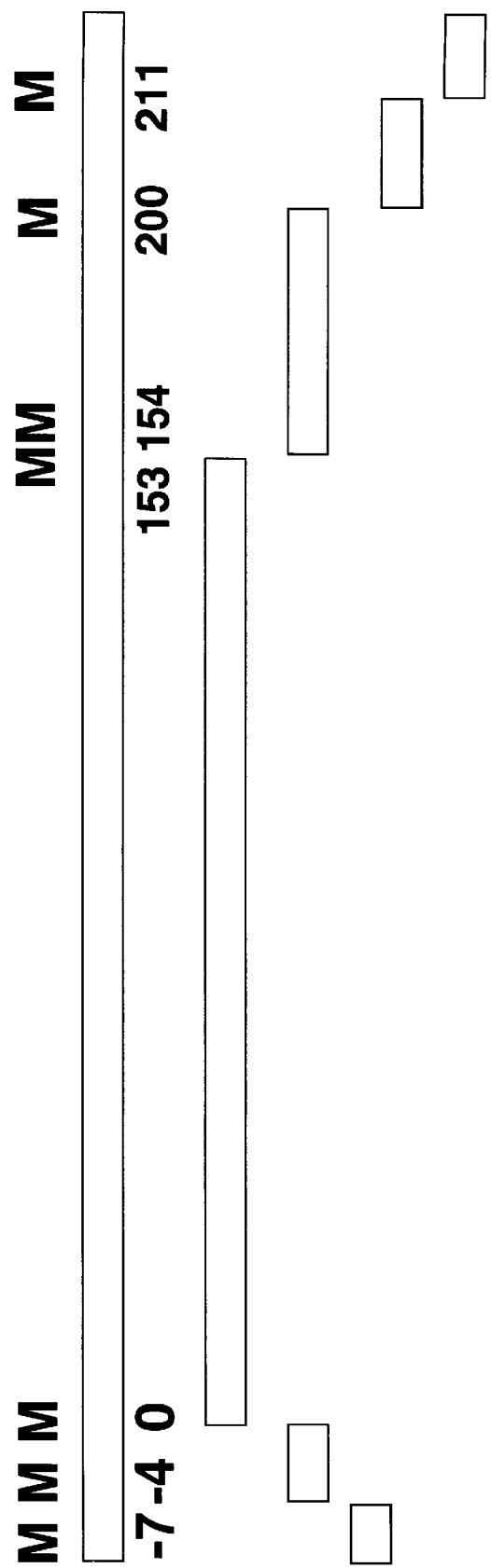
FIG. 14 depicts the CNBr cleavage strategy of r-TnI; (M)=methionine.

Cyanogen bromide cleaves at methionine residues with high specificity under acidic conditions. Cleavage of the r-TnI by CNBr at all methionine sites should produce 6 peptides of various sizes (SEQ ID NO: 5), (SEQ ID NO: 3), (SEQ ID NO: 8), (SEQ ID NO: 6), (SEQ ID NO: 7), (SEQ ID NO: 9). (See FIG. 14).

The first step is to carboxymethylate the cysteine residues (there are two in the TnI sequence) (SEQ ID NO: 1) at positions 79 and 96 in order to prevent dimerization by inter or intra molecular disulfide bridges. CNBr treatment is carried out on the carboxymethylated r-TnI. Unlike other possible cleavage reactions (e.g. enzymatic), the CNBr treatment removes the tail sequence, the leading sequence, and part of the TnI C-terminal region without affecting the primary sequence of the immunogenic sites.

Protein concentration was determined by Bradford assay (Bradford, M. M. (1976) *Anal. Biochem*. 72:248–254). SDS polyacrylamide gel electrophoresis and Western blotting analysis were performed on Mini Protean II (Biorad). The immunodetection by Western blot was carried out enzymatically using alkaline phosphatase substrate or horse radish peroxidase chemiluminescence substrate (ECL kit, Amersham). Troponin I immunoassay was carried out on the STRATUS® TI Immunoassay System (Dade International, Inc.).

The materials for SDS-PAGE, alkaline phosphatase substrate and PVDF membrane were purchased from BioRad. Anti-TnI antibodies 3D11.11, 1D12.6, 2B1.9 and 2F6.6 were obtained in accordance with the procedures described in Bodor, et al. (1992). Anti-TnT Ab and Anti-TnC Abs were commercially obtained (Vital products). Goat Anti-mouse IgG-IgM (H+L) antibody (peroxidase conjugated) was obtained from Jackson ImmunoResearch. Latex beads LB-8 (10%), carboxylate-modified latex beads L-1398 (10%), Nonidet P-40, Tricine and Tween 20 were purchased from Sigma.

Western blot analysis was carried out using either (1) anti TnI Ab-ALP (Alkaline phosphatase) or (2) Anti-TnI Ab (any preferred Abs mentioned above) as a first antibody and a goat Anti mouse IgG conjugated to alkaline phosphatase or horseradish peroxidase as a second antibody. Western analysis can be run under a range of conditions as known in the art. However, for specific detection, preferably anti-TnI Abs are used.

Example I

Coupling of TnI Antibodies to Latex Beads

TnI antibodies were immobilized on latex beads (polystyrene, 0.8 μm) (Sigma, LB-8) by:
1. Physical Adsorption.

The latex beads were diluted 20-fold with 0.1 M sodium phosphate buffer pH 6 (the coating buffer) to give a 0.5% suspension. The suspension was centrifuged twice at 10,000 rpm for 5 min. and the pellet resuspended in the same volume of buffer.

The antibodies (0.1–0.2 mg/ml) were incubated with the latex beads 0.5% suspension for 2 h at room temperature. The beads coated with antibodies settle out of solution.

The supernatant was removed and the settled beads were resuspended in 1 mL of 20 mM tris-HCl pH 7.2, 150 mM NaCl (TBS). The mixture was centrifuged at 5,000 rpm for 5 min. This process was repeated 3 times. The Ab-coated beads were then resuspended to a concentration of 0.5% in TBS containing 0.1% BSA and 0.05% $NaN_3$ and stored at 4° C. until use.

2. Covalent Attachment:

TnI antibodies were covalently attached to the latex beads.

Water soluble 1-Ethyl-3 (3-dimethylaminopropyl) carbodiimide (EDC) was employed to covalently attach antibody to carboxylated polystyrene (Jolly, M. E. (1984) *Pandex Research Report* No. 4). Specifically;

1) Carboxylated modified polystyrene latex beads (average diameter 0.9 μm) (Sigma, CLB-9) were used, and
2) Solid EDC was added to the mixture of antibody and beads in coating buffer at a concentration of 1 mg/ml and the mixture was incubated for 2 h at room temperature with shaking.

Blank beads were prepared as described above except no antibody was present.

Example II

Extraction of TnI from Serum

30–50 μL of TnI Ab coated beads suspension was added to MI patient serum (0.5–1 ml, containing 50–100 ng/ml TnI, as determined by STRATUS® TnI Immunoassay). The mixture was incubated at room temperature for 30 min. After incubation, the mixture was centrifuged at 8,000 rpm for 5 min. The supernatant was tested to determine the amount of TnI extracted. The pellet was resuspended in TBS and centrifuged at 8,000 rpm for 5 min twice. The TnI fragments were eluted by incubating the beads in either:

1. Electrophoresis sample buffer containing SDS (25–50 μL) overnight at room temperature. The sample was centrifuged at 8,000 rpm for 5 min and the supernatant kept for analysis by Western blot; or
2. Buffer containing urea (25–50 μL), 100 mM sodium phosphate, 10 mM tris and 8 M urea (pH 8) (PTU). The suspension was incubated overnight at room temperature. The sample was centrifuged at 8,000 rpm for 5 min and the supernatant was kept for analysis by Western blot.

Example III

Extraction of Fragments from MI Patient Serum

The following TnI antibodies, 3D11.11, 1D12.6, 2B1.9 and 2F6.6 (Bodor, G. S., et al, 1992) *Clin. Chem.* 38: 2203–2214) were separately immobilized on latex beads according to either of the above methods. TnI was extracted from MI patient serum according to the methods described above.

Figure 2A:
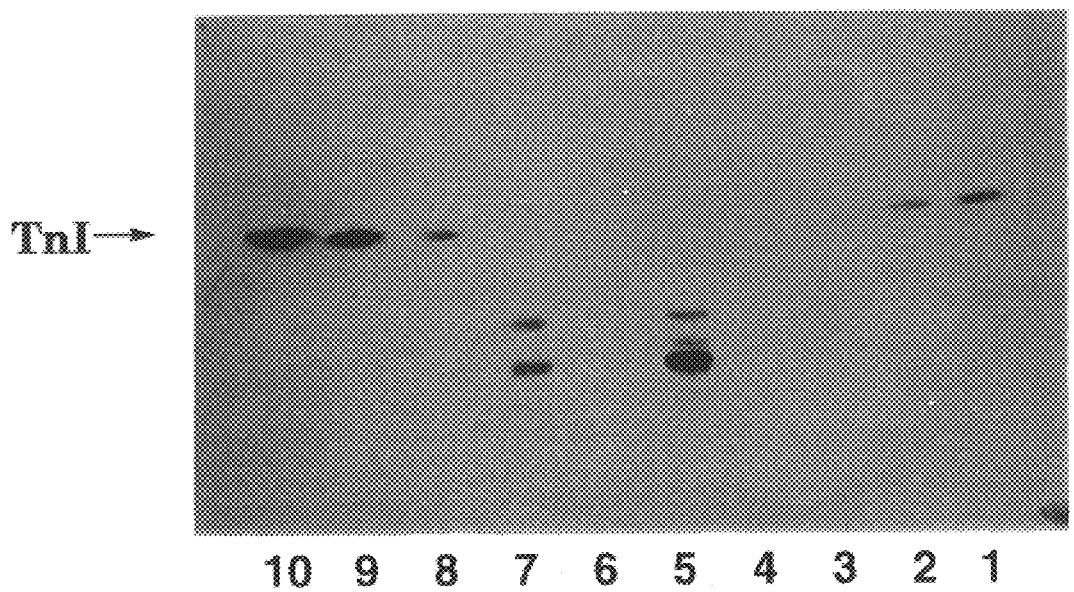
FIG. 2a and 2b show the immunoreactivity of cTnI in MI patient serum pool extracted by latex beads coated with anti TnI monoclonal antibodies.

FIG. 2a shows the Western blot analysis of MI patient serum pools extracted with various beads containing TnI antibodies and probed with 2B1.9 Ab. Lanes 1, 2, 8, 9 and 10 contained bovine cardiac TnI controls. Lane 3 contained MI patient serum extracted using blank beads (no Ab). Lane 4 contained MI patient serum extracted using 3D11.11 Ab. Lane 5 contained MI patient serum extracted using 2B1.9 Ab. Lane 6 contained MI patient serum extracted using 2F6.6 Ab. Lane 7 contained serum extracted using 1D12.6 Ab. Samples were run on 15% SDS-PAGE, transferred to PVDF membrane and probed by anti TnI Ab 2B1.9. FIG. 2a shows little intact TnI in the samples extracted from MI patient serum (Lanes 5, 6 and 7). However, two major bands with lower molecular weights (apparent MW 14,000 and 18,000) were detected. Similar results were obtained when the TnI antibody 2F6.6 was used to probe for TnI.

Figure 2B:
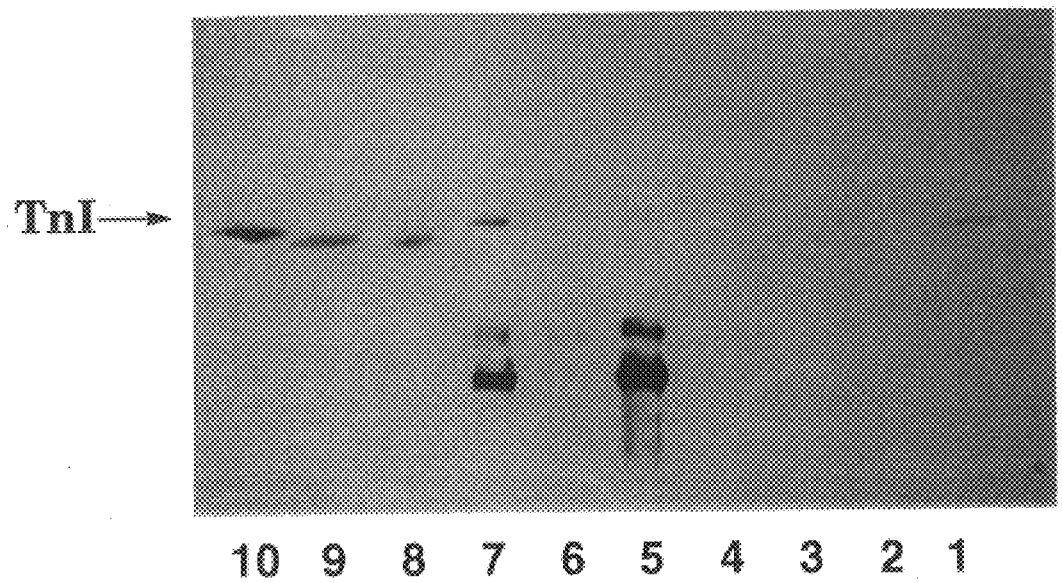

FIG. 2b shows the immunoreactivity of MI patient serum pool extracted by latex beads coated with anti TnI monoclonal antibodies and probed with TnI antibody 2F6.6. In FIG. 2b, lane 1 contained bovine cardiac TnI. Lane 2 was empty. Lane 3 contained MI patient serum extracted using blank beads (no Ab). Lane 4 contained MI patient serum extracted using 3D11.11 Ab. Lane 5 contained MI patient serum extracted using 2B1.9 Ab. Lane 6 contained MI patient serum extracted using 2F6.6 Ab. Lane 7 contained MI patient serum extracted using 1D12.6 Ab. Lanes 8, 9 and 10 contain bovine cardiac TnI. Samples were run on 15% SDS-PAGE, transferred to PVDF membrane and probed by anti TnI Ab 2F6.6.

This method extracted from about 70 to about 98% of TnI from MI patient serum when using 1D12.6, 2B1.9 and 2F6.6 antibodies. The beads containing 3D11.11 antibody performed similarly to the control (beads without antibody). The antibody 3D11.11 failed to extract or detect TnI fragments.

The above results indicate that MI patient serum TnI is processed primarily from the C-terminal end.

Example IV

TnI Processing in MI Patient Serum

In order to understand the mechanism of TnI processing in MI patient serum, serum samples taken from individuals were examined at different times after MI.

Figure 3A:
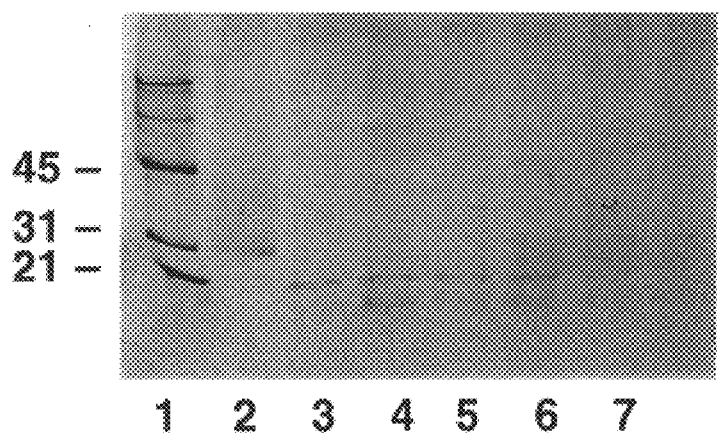
FIG. 3a–3c shows immunological detection of TnI in individual patient serum samples taken at varying time intervals after MI.
Figure 3B:
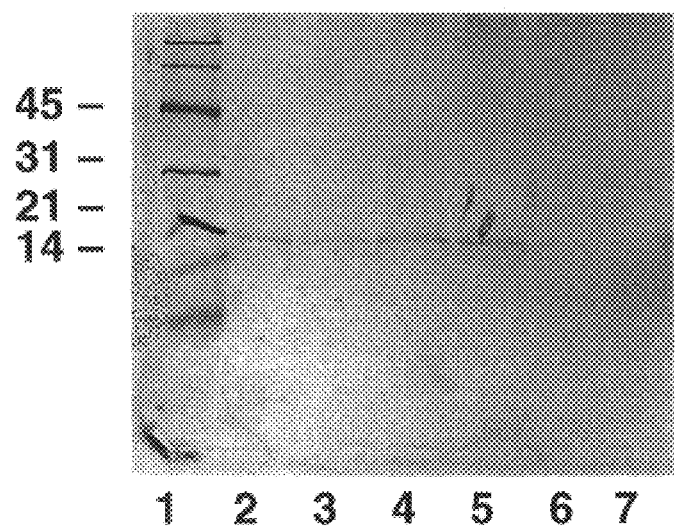
Figure 3C:
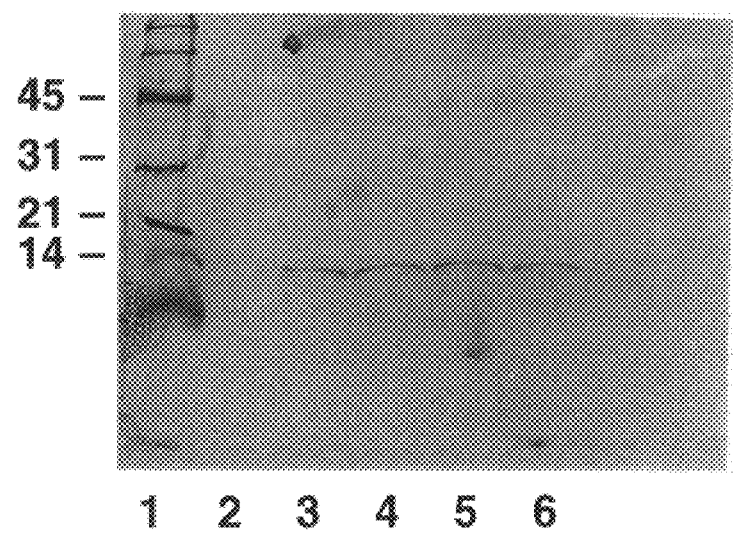

These samples were extracted by beads coated with 2B1.9 Ab and analyzed by Western blot. The results are shown in FIG. 3A–3C. In FIG. 3a, lane 1 contains a molecular weight standard. Lane 2 contains r-TnI. Lanes 3 to 7 contain extracted serum samples taken from a patient (LM) 1 and 5 days after MI. In FIG. 3b, lane 1 contains a molecular weight standard. Lane 2, 3 and 4 contain serum samples taken from a patient (CE) at 2, 3 and 4 days after MI. Lanes 5 and 6 contain serum samples taken from a patient (RW) 1 and 2 days after MI. In FIG. 3c, lane 1 contains a molecular weight standard. Lane 2 contains r-TnI. Lanes 3 to 6 contain serum samples taken from a patient (RH) 2, 4, 5, and 6 days after MI.

These results demonstrate that both TnI fragments or either one alone are present in serum of MI patients. The results suggest that the two bands are generated by sequential processing of the TnI molecule. N-terminal processing of TnI was also seen.

The lower molecular weight TnI fragment was isolated from a pool of patient serum and sequenced for N-terminal identification. FIG. 4a shows alignment of the N-terminal of TnI fragment with intact human TnI. The N-terminal sequence of the TnI fragment starts at position 27 (Ala) in intact human cardiac TnI. FIG. 4b shows a western blot of the lower molecular weight TnI fragment (see FIG. 3) isolated from MI patient serum.

FIG. 5 shows a schematic representation for processing of MI patient serum TnI.

Example V

In vitro Degradation of TnI in Normal Human Serum (NHS) and Patient Serum Depleted of TnI After spiking into serum, the recovery and degradation of both human recombinant TnI (r-TnI) and bovine cardiac TnI was followed at 23° C. over 5 days. Aliquots were taken and tested for TnI activity using STRATUS® TnI immunoassay and for TnI immunoreactivity by Western blot.

FIGS. 6a and 6b depict the degradation of r-TnI and bovine TnI in normal human serum, respectively. TnI was spiked into serum and incubated at room temperature. Aliquots were taken and kept at −22° C. until analysis. The samples were analyzed by Western blot (SDS-PAGE, 15%) using the STRATUS® II conjugate antibody.

Figure 7:
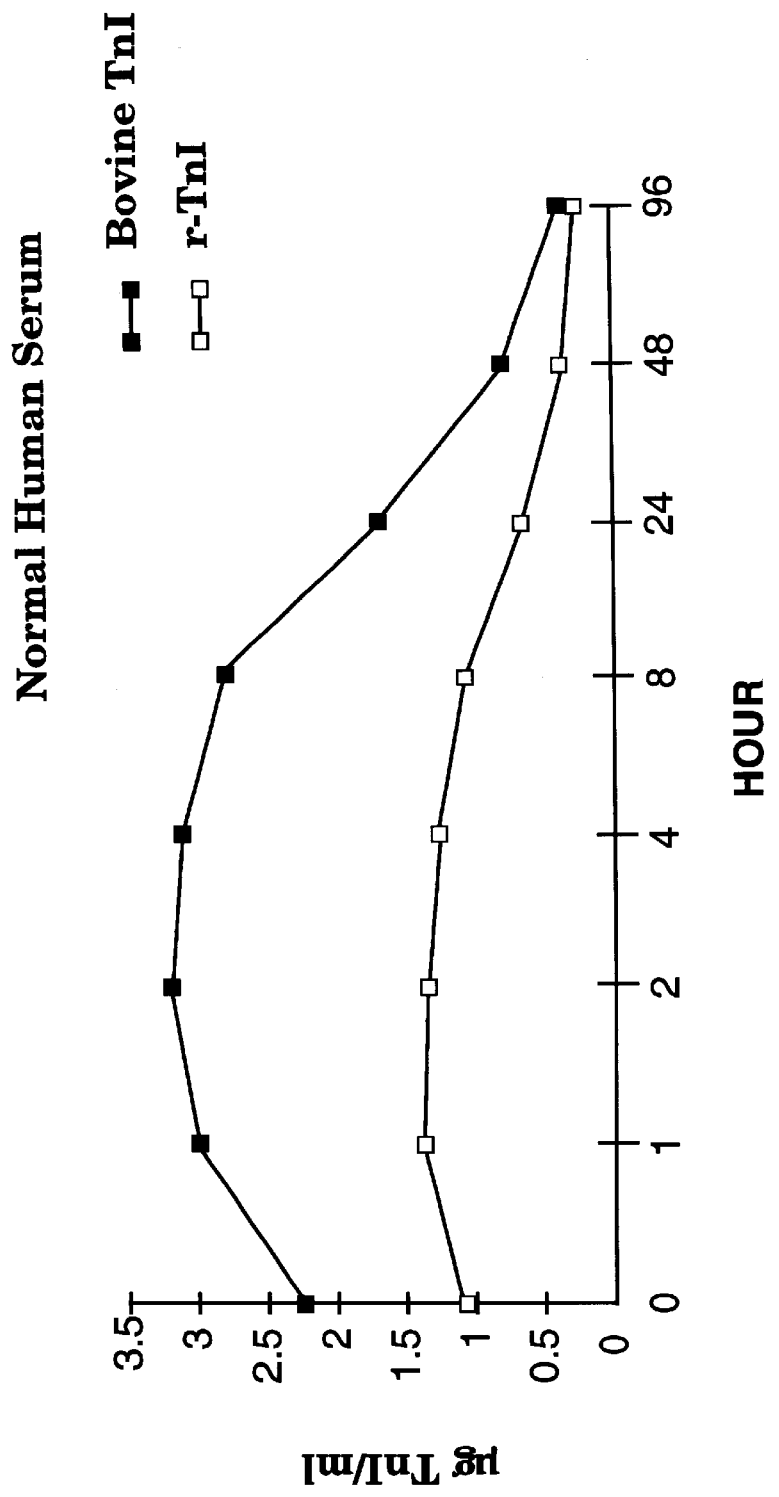
FIG. 7 shows stability of bovine cardiac TnI (■) and human r-TnI (⊠) in normal human serum.

Both proteins degrade to lower molecular weight species after spiking into serum. Recombinant TnI appears to be more susceptible to degradation than bovine TnI. The TnI activity increased after 1 hour incubation in serum followed by stable recovery over the following 8 h. After 8 h incubation, the TnI activity was rapidly lost, as shown in FIG. 7. FIG. 7 shows stability of bovine cardiac TnI (■) and human r-TnI (□) in normal human serum. TnI was spiked into normal human serum at 3.2 μg/ml and the mixtures were incubated at room temperature. Aliquots were withdrawn and tested for activity using STRATUS® TnI Immunoassay.

Figure 8A:
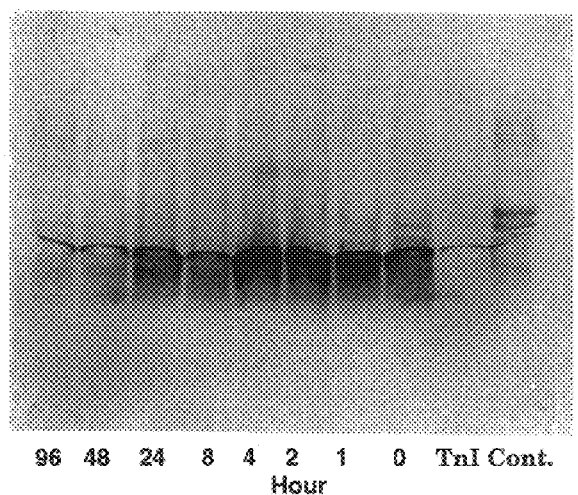
FIG. 8a–8b shows degradation of bovine TnI(A) and human rTnI(B) in MI patient serum depleted of TnI.
Figure 8B:
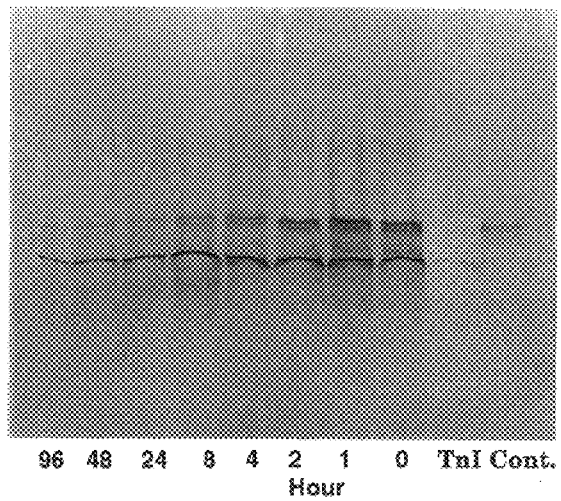

Similar degradation patterns were seen when bovine TnI or rTnI were spiked into pooled MI patient serum depleted of TnI (FIG. 8A–8B). TnI was spiked into serum and incubated at room temperature. Aliquots were taken and kept at −22° C. until analysis. The samples were analyzed by Western (SDS-PAGE, 15%) using STRATUS® II conjugate antibody (FIG. 8A–8B). The band seen in the control lane (lane 2) most likely is residual endogenous TnI, present in the pooled patient serum.

Figure 9:
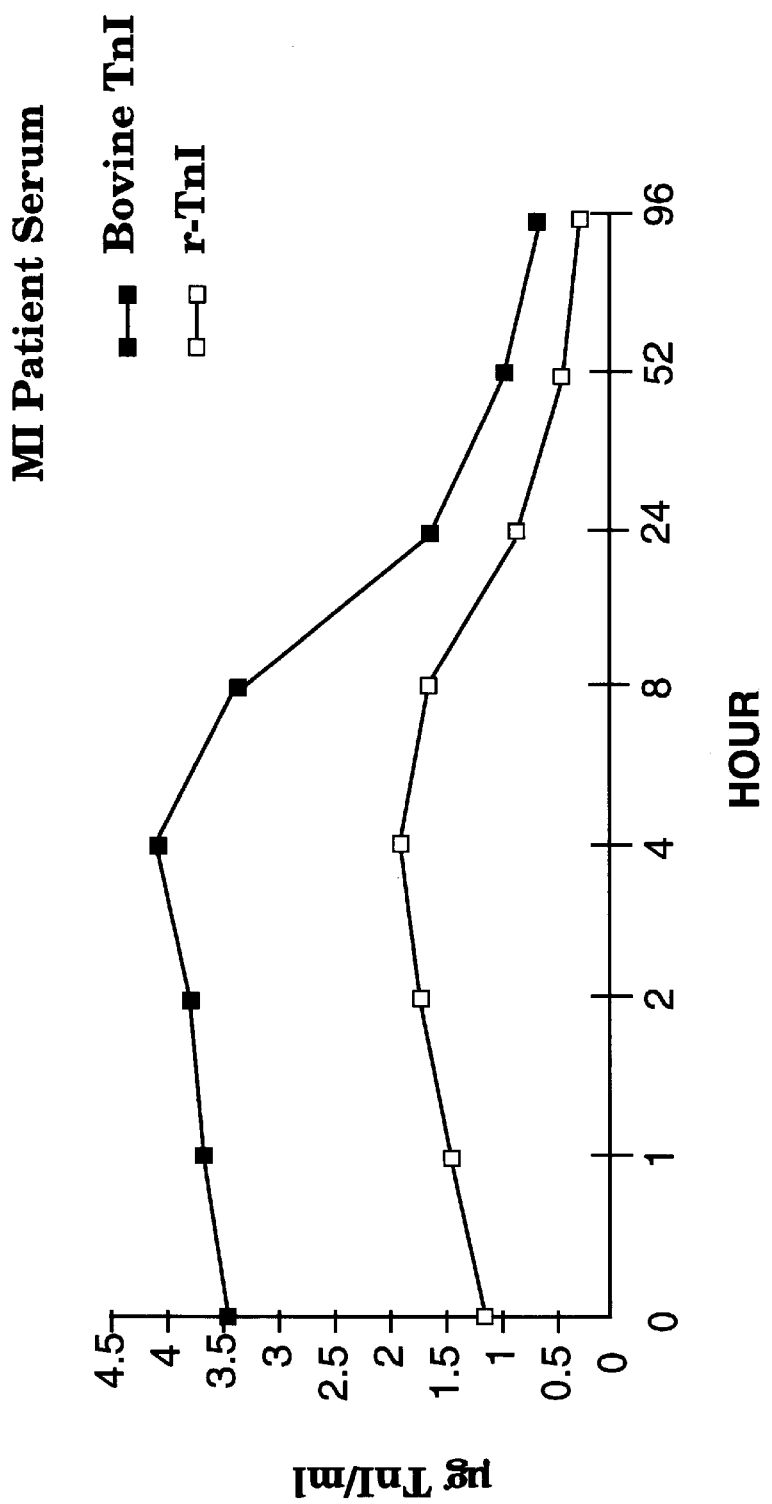
FIG. 9 is a graph that shows stability of bovine TnI (■) and human r-TnI (⊠) in MI patient serum depleted of TnI.

The results are graphically shown in FIG. 9. In MI patient serum depleted of TnI, the TnI activity of both bovine TnI and r-TnI increased gradually in the first four hours after spiking, followed by rapid loss of activity (FIG. 9, bovine TnI (■) and human r-TnI (□) in MI patient serum depleted of TnI). In FIG. 9, TnI was spiked into MI patient serum at 3.2 μg/ml and the mixtures were incubated at room temperature. Aliquots were withdrawn and tested for activity by STRATUS® TnI Immunoassay.

It is not presently known whether TnI processing happens in heart cells or after being released into circulation. Analysis of TnI extracted from patient serum samples taken after MI is shown in FIG. 3A–3C. The results suggest that degradation of TnI occurs in the heart cells before it gets released into circulation. TnI may, however, undergo processing after being released into circulation. The difficulty of obtaining serum samples during or immediately after chest pain thus far has made it difficult to determine where TnI degradation occurs. The samples analyzed have been taken after admitting the patients to a hospital, but this could be days after MI.

Example VI

Protease Testing

To test TnI sensitivity to proteases, rTnI or bovine TnI at 0.25 mg/ml was digested with 1% papain at 37° C. At set time intervals, aliquots were withdrawn and the reaction was stopped by adding electrophoresis sample buffer. Numbers indicate the length of incubation in minutes. The digests were run on SDS-PAGE under reducing conditions.

Figure 10:
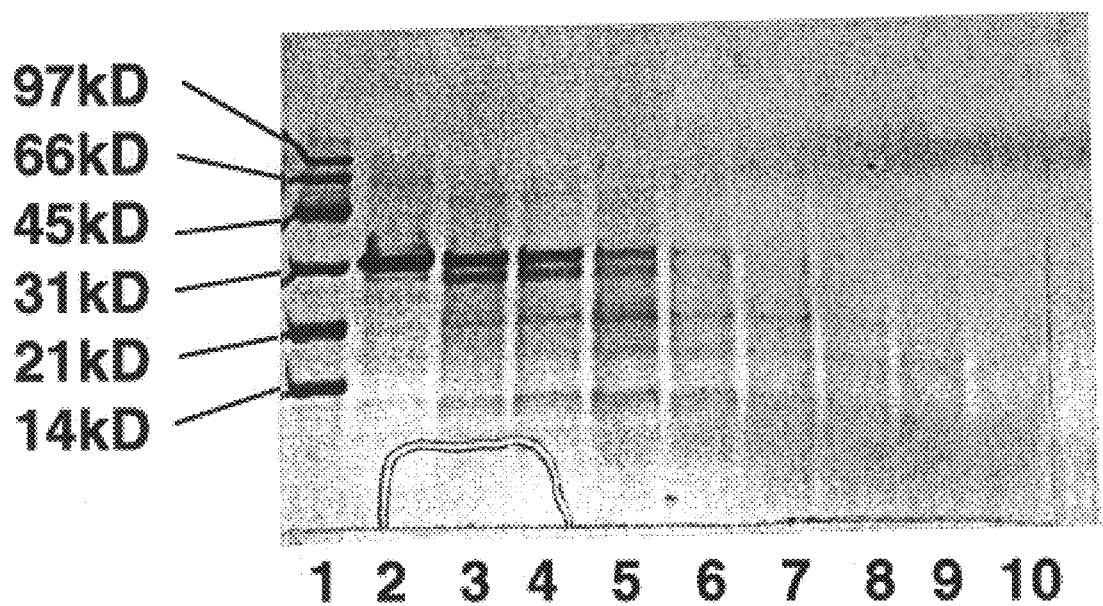
FIG. 10 shows degradation of TnI by papain.

FIG. 10 shows the fast disappearance of the intact TnI molecule and the appearance of lower molecular weight fragments. A number of protease inhibitors, selected for broad spectrum of inhibition, were used to prevent TnI degradation in serum (not shown). Addition of these inhibitors to normal human serum before spiking with TnI did not prevent TnI degradation.

Example VII

Extraction of TnI Complex

The extraction procedure of MI patient serum was modified to investigate the possible association between TnI and other Tn subunits. Troponin I extracted from patient serum was released from the beads according to the methods described above, except, in the absence of SDS.

Figure 11A:
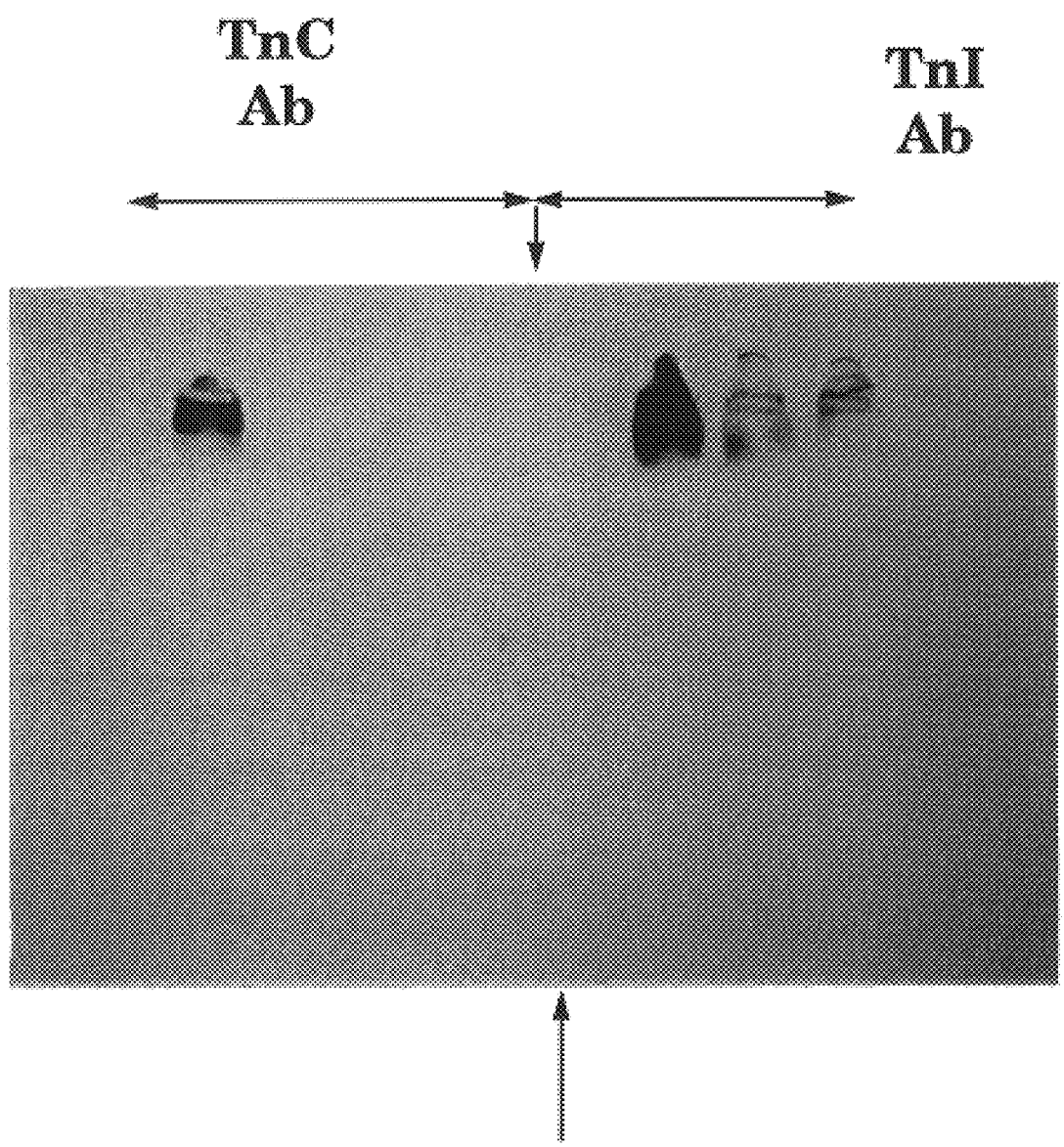
FIG. 11a–11b shows detection of troponin complex in MI patient serum.

A MI patient serum pool with high level of TnI immunoassay activity was incubated with latex beads coated with anti-TnI Ab 2B1.9. The bound TnI was eluted using buffer containing 8 M urea. The isolated TnI was run on polyacrylamide gel electrophoresis (native gel, 10%, no SDS) and transferred to a PVDF membrane. The membrane was cut in two: one probed by anti TnI Ab and the second by anti TnC Ab. The results are shown in FIG. 11a.

Figure 11B:
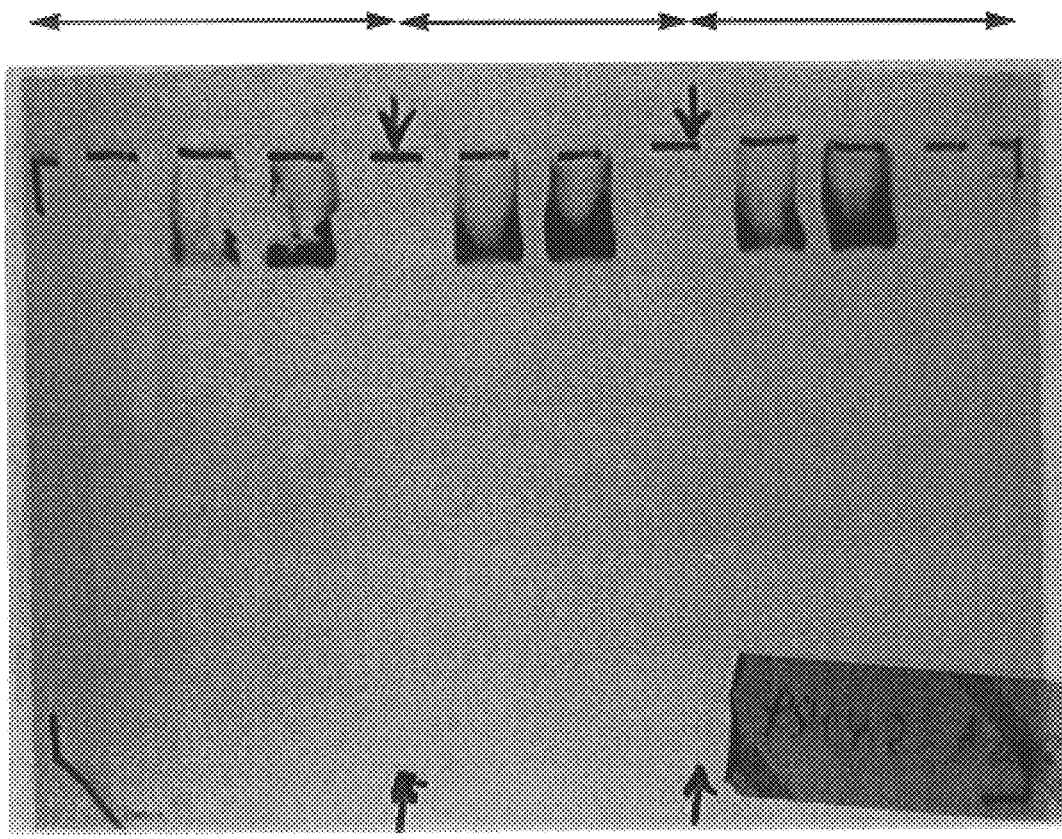

Samples from the same extract were run in duplicate on a native gel and transferred to PVDF membrane. The membrane was cut into 3 parts each containing duplicates of the extract. Each part was probed separately by anti-TnC, anti-TnI or anti-TnT antibodies. The three different antibodies recognized a single band with comparable mobility suggesting that the isolated species contains the three troponin subunits TnI, TnC and TnT. (FIG. 11b).

Example VIII

Comparison of Human TnI Forms

Figure 17:
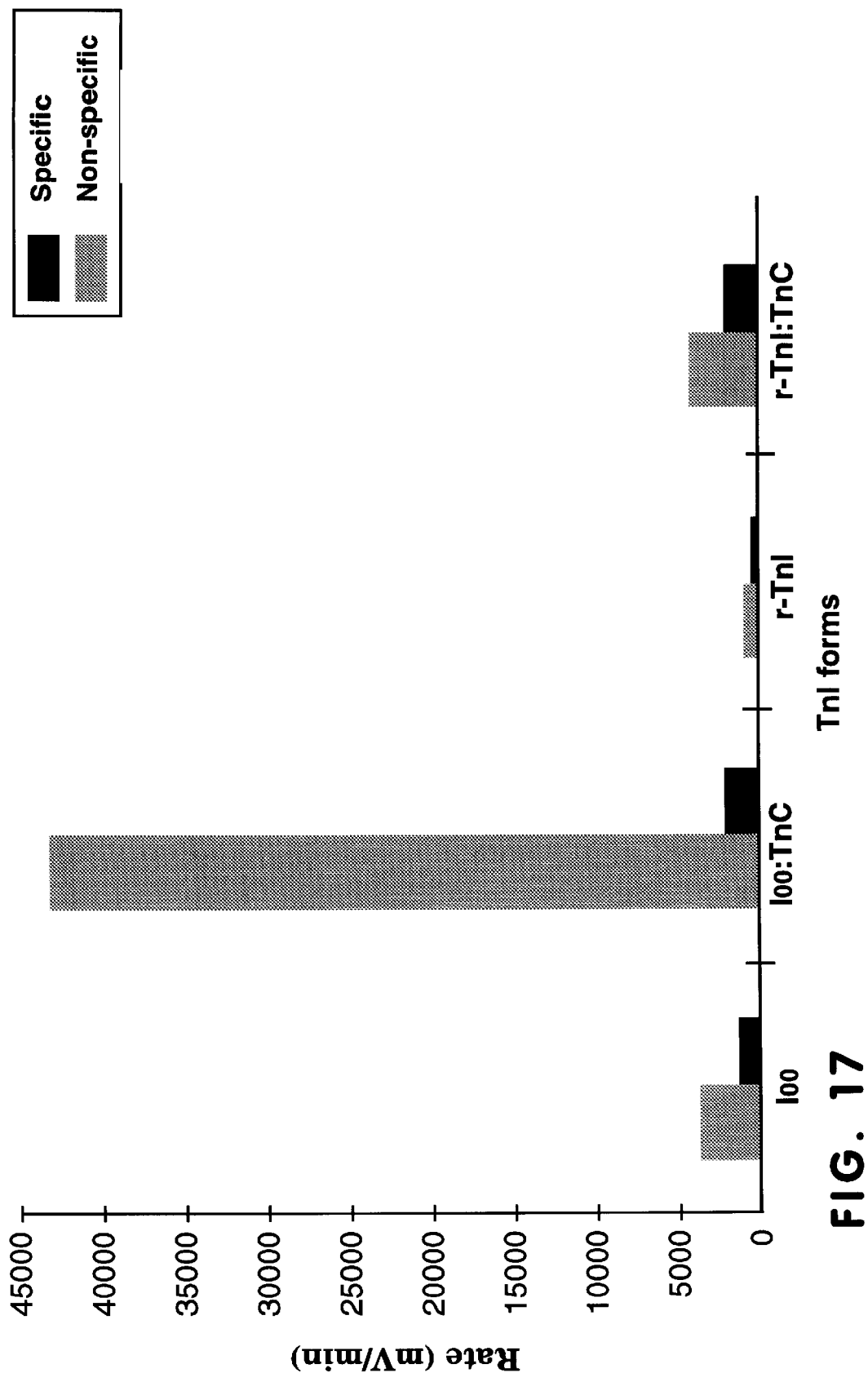
FIG. 17 shows the activity and non-specific binding of various TnI preparations.

The activity of fragments of r-TnI were compared.
A. Preparation of and Properties of a TnI 88 Amino Acid-cIsoform II cIsoform II was generated from r-TnI (see FIG. 13) using the endoproteinase Asp-N ("EndoAsp"). EndoAsp, a metalloprotease, cleaves at the N-terminus of aspartic acid. Recombinant TnI was incubated with EndoAsp at a ratio of 100:1 (r-TnI:EndoAsp, w/w) in 50 mM sodium phosphate pH 8 containing 1 M urea for 20 hours at 37° C. The major cleavage product consisted of 88 amino acids starting at position 6 (Aspartic acid, D) and ending at position 95 (Glutamine, Q) (FIG. 13) (SEQ ID NO: 10) ("TnI88"). FIG. 13 depicts the alignment of the human cardiac Troponin I amino acid sequences. Single letter code has been used. Other symbols include: (r)=r-TnI (SEQ ID NO: 1); (h) native human cTnI (SEQ ID NO: 2); (I)-CNBI-CTnT isoform (SEQ ID NO: 3); (cam)=S-carboxyamidomethylcysteine. Once purified, the cisoform II was tested for purity and activity on SDS-polyacrylamide gel electrophoresis and the Stratus® II TnI Immunoassay System, respectively. Non-specific binding was tested using Ferritin tabs. As shown in FIG. 17, the cIsoform II has higher activity (2-fold) and higher non-specific binding (2-fold) than the CNBr-cTnI isoform. However, little enhancement in TnI activity of cIsoform II was seen when it was incubated with TnC in the presence of 2 mM $CaCl_2$.

B. Preparation of CNBr-cTnI Isoform (TnI153)

Three trial preparations of the CNBr-cTnI isoform were conducted. Recombinant TnI (10–20 mg., 0.25–0.3 mM) in 100 mM Na-phosphate, 10 ThM tris, 8 M urea, pH 8 ("PTU buffer") was reduced by adding sufficient Dithiothreitol (DTT) freshly prepared in the same buffer (200 mM stock solution) to give a final concentration of 2.5 mM of DTT. The mixture was incubated at room temperature (approximately 23–25° C.) for a time sufficient to reduce the rTnI (approximately 1 hour). The reduced r-TnI was treated with iodoacetamide(prepared in the PTU buffer, 400 mM stock solution) to give a final concentration of 15 mM of iodoacetamide in the reaction mixture. The mixture was then incubated for a time and under conditions sufficient to complete the carboxymethylation reaction (approximately 1 hour) in the dark at 37° C.

The mixture was transferred to 10×25 mm wide spectra/por (12–14 kd MWCO) dialysis tubing and dialyzed against 2×1L of 25% acetic acid for 24 hours at room temperature, with stirring.

The dialyzed cTnI was lyophilized under vacuum (<1 mm Hg) between room temperature and 45°. The lyophilized rTnI was dissolved in approximately 1.4 ml 70% formic acid and then CNBr (1 ug/uL in 70% formic acid) was added to the rTnI solution to give a final concentration of 480 mM of CNBr (approximately 160 mol CNBr/mol methionine). The tube containing the reaction mixture was purged with nitrogen and then incubated at least 16 hours at room temperature in the dark with rocking. The reaction was stopped by adding distilled water to give 1:10 dilution of the digest. The digest was lyophilized under vacuum (<1 mm Hg) between room temperature and 45° C. The lyophilized digest was dissolved in a minimum volume of 88% formic acid. The digest was applied on a Sephadex G-200 (1.6×100 cm) column equilibrated with 25% acetic acid. The CNBr-cTnI isoform was eluted with 25% acetic acid. The first major peak, which represented the CNBr-cTnI isoform, was pooled and tested for purity by SDS-PAGE and for immunoreactivity by the Stratus® II TnI Immunoassay System.

Figure 15:
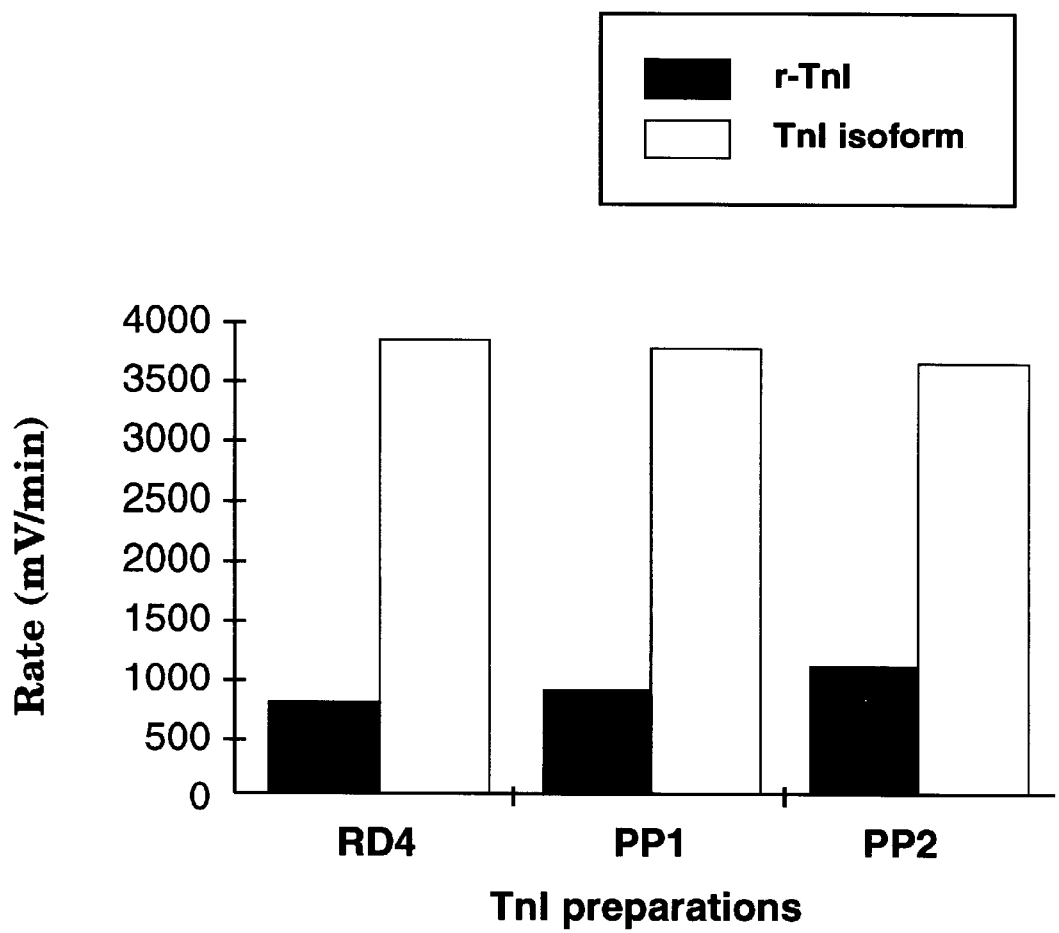
FIG. 15 shows the activity of r-TnI and CNBR-cTnI isoform in calibrator base as measured with the Stratus® II TnI Immunoassay System.
Figure 16:
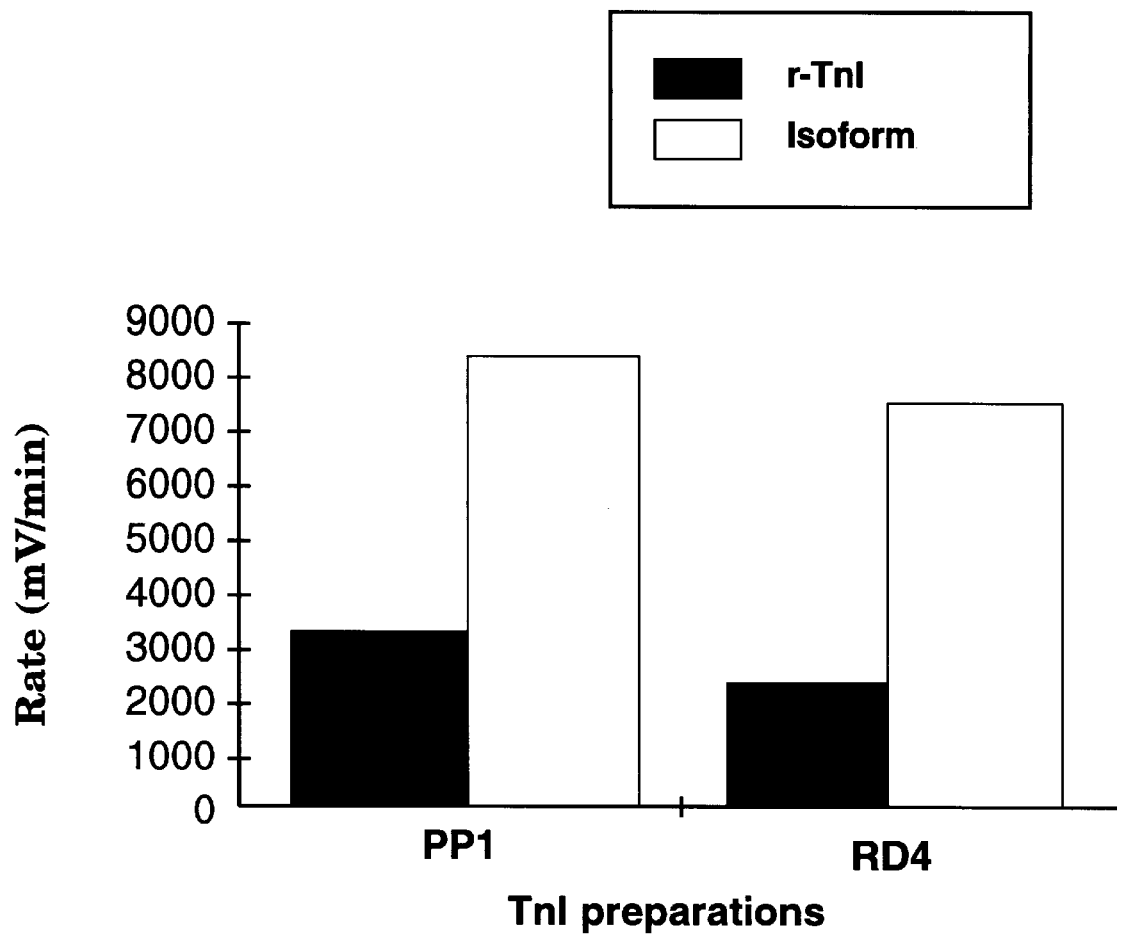
FIG. 16 depicts the activity of r-TnI and the CNBr-cTnI isoform in human serum as measured with the Stratus® II TnI Immunoassay System.

As measured by the Stratus® II TnI Immunoassay System, the purified CNBr-cTnI isoform has 3–4 fold higher immunological activity than r-TnI (See FIGS. 15 and 16).

As disclosed in copending application Ser. No. 08/564, 526, the purified CNBR-cTnI isoform migrates on SDS-PAGE gel electrophoresis as a single band with an apparent molecular weight of 21,000 daltons. Western blot analysis of the CNBr-cTnI isoform has a molecular weight close to that of a major degradation fragment of cTnI in MI patient serum. The N-terminal sequence analysis of the isoform gave the sequence Ala-Asp-Gly-Ser-Ser-Asp-Ala-Ala-Ala-Arg-Glu, which is identical to the N-terminal sequence of human cTnI (SEQ ID NO: 2). Amino acid analysis confirms that the purified CNBr-cTnI isoform represents the first 153 amino acids of the cTnI molecule. (SEQ ID NO: 1.)

Figure 12:
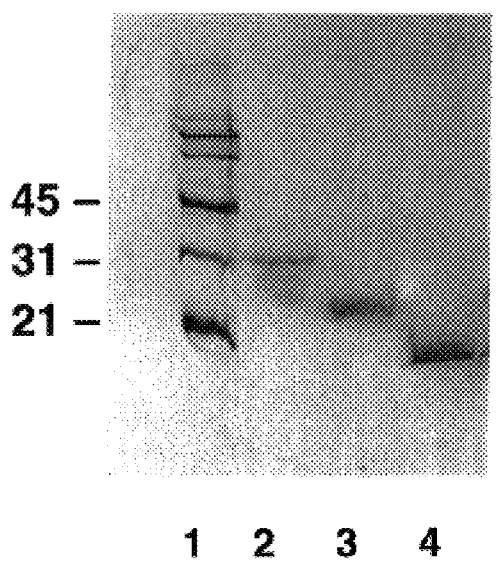
FIG. 12 shows a Western blot analysis of human TnI forms from recombinant TnI.

C. Western Blot of Isoforms:

Samples (25–50 ng) of each of rTnI, TnI153 and TnI88 were western blotted as shown in FIG. 12. Lane 1 contained a molecular weight standard. Lane 2 contained intact recombinant TnI (rTnI). Lane 3 contained the CNBr TnI isoform ("TnI153")(from amino acid 1–153 of SEQ ID NO:2). Lane 4 contained TnI isoform II ("TnI88")(from amino acid 6–95 of SEQ ID NO: 2).

Furthermore, the relationship between TnI fragment length and activity was analyzed by measuring activity using the STRATUS® II Immunoassay System (Dade International Inc.). 40 nM of each of rTnI, TnI153 and TnI88 were added to calibrator base containing BSA. The results are shown in Table 2.

TABLE 2

| FORM | ACTIVITY (mV/min) |
| --- | --- |
| rTnI | 849 |
| TnI153 | 5762 |
| TnI 88 | 11783 |

As shown in Table 2 and FIG. 12, the activity of the fragments is significantly greater than the activity of the intact TnI molecule. As shown in Table 2, the smaller fragment, TnI 88 is more active than TnI153. This data shows that TnI fragments are more active than intact TnI in vivo.

Example IX

The cTnI Fragment as a Calibrator and a Control

A. Preparation of Controls:

A stock solution of the cTnI fragment (1 mg/ml) was prepared in 100 mM sodium phosphate buffer pH 8 containing 10 mM tris and 8 M urea using polypropylene tubes. A liquid tri-level assay control containing the cTnI fragment was prepared in serum, diluted serum, plasma, diluted plasma or control base using plastic labware. Any type of control base can be used. Preferably the base is a buffer containing BSA. For example, a preferred base used contained contains 9.5% protease free BSA, 8.18 mM EDTA, 0.1% bovine gelatin, 50 mM sodium phosphate, 700 mM sodium chloride, 5% Trehalose, 3 ppm Clotrimazole (antibacterial agent), 163 ppm chloramphenicol, 2.58 mM N-acetyl-cysteine, at pH 7.3. Alternatively, 2 mm $CaCl_2$ may be used in place of the EDTA. Optionally, 0.5% sodium azide can be added.

Alternatively, instead of a buffer, the fragments were spiked into serum, e.g., human or bovine, or into diluted serum, e.g., serum diluted 1:1 with MES buffer containing BSA.

The levels of controls were:

| Manufacturing Ranges | cTnI Range (ng/ml) |
| --- | --- |
| Level 1 | 3–6 |
| Level 2 | 17–22 |
| Level 3 | 35–44 |

CTnI fragment stock solution was spiked into serum, diluted serum, plasma, diluted plasma or base at the designated level. The mixtures are filtered and tested on the Stratus® II Immunoassay System for the matching of TnI concentration. Preparation of each level (3 ml each) were placed in plastic vials which were either stored at 4° C. or lyophilized. The lyophilized material was reconstituted using 3 ml of water upon use.

B. Preparation of Calibrators:

The calibrators were made by adding a sufficient amount of cTnI fragment stock solution to serum, plasma or base, to give final concentrations ranging from 2 to 50 ng/ml. The cTnI fragment calibrator concentrations were 0 ng/ml, 2 ng/ml, 8 ng/ml, 15 ng/ml, 25 ng/ml and 50 ng/ml. Preferably the base is a buffer containing BSA. For example, a preferred base used contained contains 9.5% protease free BSA, 8.18 mM EDTA, 0.1% bovine gelatin, 50 mM sodium phosphate, 700 mM sodium chloride, 5% Trehalose, 3 ppm Clotrimazole (antibacterial agent), 163 ppm chloramphenicol, 2.58 mM N-acetyl-cysteine, at pH 7.3. Alternatively, 2 mm $CaCl_2$ may be used in place of the EDTA. Optionally, 0.5% sodium azide can be added.

Alternatively, instead of a buffer, the fragments were spiked into serum, e.g., human or bovine, or into diluted serum, e.g., serum diluted 1:1 with MES buffer containing BSA.

Each calibrator level was filtered and analyzed on the Stratus® II Immunoassay System using TnI immunoassay and matched against the reference level. The calibrators were then filled into their designated vials and either lyophilized or stored at 4° C. The lyophilized calibrators were reconstituted to the pre-lyophilization volume using water.

The invention has been described in detail with particular reference to the preferred embodiments thereof. However, it will be appreciated that modifications and improvements within the spirit and teachings of this inventions may be made by those in the art upon considering the present disclosure.

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 226 amino acids
      (B) TYPE: amino acid
      (C) STRANDEDNESS: single
      (D) TOPOLOGY: linear (xi) SEQUENCE DESCRIPTION: SEQ ID NO:1:

Met Ala Ser Met Thr Leu Trp Met Ala Asp Gly Ser Ser Asp Ala Ala
1               5                   10                  15

Arg Glu Pro Arg Pro Ala Pro Ala Pro Ile Arg Arg Ser Ser Asn
            20                  25                  30

Tyr Arg Ala Tyr Ala Thr Glu Pro His Ala Lys Lys Ser Lys Ile
            35                  40                  45

Ser Ala Ser Arg Lys Leu Gln Leu Lys Thr Leu Leu Leu Gln Ile Ala
50                  55                  60

Lys Gln Glu Leu Glu Arg Glu Ala Glu Glu Arg Arg Gly Glu Lys Gly
65                  70                  75                  80

Arg Ala Leu Ser Thr Arg Cys Gln Pro Leu Glu Leu Thr Gly Leu Gly
                85                  90                  95

Phe Ala Glu Leu Gln Asp Leu Cys Arg Gln Leu His Ala Arg Val Asp
            100                 105                 110

Lys Val Asp Glu Glu Arg Tyr Asp Ile Glu Ala Lys Val Thr Lys Asn
            115                 120                 125

Ile Thr Glu Ile Ala Asp Leu Thr Gln Lys Ile Phe Asp Leu Arg Gly
            130                 135                 140

Lys Phe Lys Arg Pro Thr Leu Arg Arg Val Arg Ile Ser Ala Asp Ala
145                 150                 155                 160

Met Met Gln Ala Leu Leu Gly Ala Arg Ala Lys Glu Ser Leu Asp Leu
                165                 170                 175

Arg Ala His Leu Lys Gln Val Lys Lys Glu Asp Thr Glu Lys Glu Asn
            180                 185                 190

Arg Glu Val Gly Asp Trp Arg Lys Asn Ile Asp Ala Leu Ser Gly Met
            195                 200                 205

Glu Gly Arg Lys Lys Lys Phe Glu Ser Pro Met Val His His His
            210                 215                 220

His His
225

(2) INFORMATION FOR SEQ ID NO:2:

(i) SEQUENCE CHARACTERISTICS:
        (A) LENGTH: 209 amino acids
        (B) TYPE: amino acid
        (C) STRANDEDNESS: single
        (D) TOPOLOGY: linear (xi) SEQUENCE DESCRIPTION: SEQ ID NO:2:

Ala Asp Gly Ser Ser Asp Ala Ala Arg Glu Pro Arg Pro Ala Pro Ala
1               5                   10                  15

Pro Ile Arg Arg Arg Ser Ser Asn Tyr Arg Ala Tyr Ala Thr Glu Pro
            20                  25                  30

His Ala Lys Lys Lys Ser Lys Ile Ser Ala Ser Arg Lys Leu Gln Leu
            35                  40                  45

Lys Thr Leu Leu Leu Gln Ile Ala Lys Gln Glu Leu Glu Arg Glu Ala
50                  55                  60

Glu Glu Arg Arg Gly Glu Lys Gly Arg Ala Leu Ser Thr Arg Cys Gln
65                  70                  75                  80

Pro Leu Glu Leu Thr Gly Leu Gly Phe Ala Glu Leu Gln Asp Leu Cys
                85                  90                  95

Arg Gln Leu His Ala Arg Val Asp Lys Val Asp Glu Glu Arg Tyr Asp
            100                 105                 110

```
Ile Glu Ala Lys Val Thr Lys Asn Ile Thr Glu Ile Ala Asp Leu Thr
            115                 120                 125

Gln Lys Ile Phe Asp Leu Arg Gly Lys Phe Lys Arg Pro Thr Leu Arg
            130                 135                 140

Arg Val Arg Ile Ser Ala Asp Ala Met Met Gln Ala Leu Leu Gly Ala
145                 150                 155                 160

Arg Ala Lys Glu Ser Leu Asp Leu Arg Ala His Leu Lys Gln Val Lys
                165                 170                 175

Lys Glu Asp Thr Glu Lys Glu Asn Arg Glu Val Gly Asp Trp Arg Lys
            180                 185                 190

Asn Ile Asp Ala Leu Ser Gly Met Glu Gly Arg Lys Lys Lys Phe Glu
            195                 200                 205

Ser
```

(2) INFORMATION FOR SEQ ID NO:3:

(i) SEQUENCE CHARACTERISTICS:
        (A) LENGTH: 153 amino acids
        (B) TYPE: amino acid
        (C) STRANDEDNESS: single
        (D) TOPOLOGY: linear (xi) SEQUENCE DESCRIPTION: SEQ ID NO:3:

```
Ala Asp Gly Ser Ser Asp Ala Ala Arg Glu Pro Arg Pro Ala Pro Ala
1               5                   10                  15

Pro Ile Arg Arg Arg Ser Ser Asn Tyr Arg Ala Tyr Ala Thr Glu Pro
            20                  25                  30

His Ala Lys Lys Ser Lys Ile Ser Ala Ser Arg Lys Leu Gln Leu
            35                  40                  45

Lys Thr Leu Leu Leu Gln Ile Ala Lys Gln Glu Leu Glu Arg Glu Ala
    50                  55                  60

Glu Glu Arg Arg Gly Glu Lys Gly Arg Ala Leu Ser Thr Arg Cys Gln
65                  70                  75                  80

Pro Leu Glu Leu Thr Gly Leu Gly Phe Ala Glu Leu Gln Asp Leu Cys
            85                  90                  95

Arg Gln Leu His Ala Arg Val Asp Lys Val Asp Glu Gly Arg Tyr Asp
            100                 105                 110

Ile Glu Ala Lys Val Thr Lys Asn Ile Thr Glu Ile Ala Asp Leu Thr
            115                 120                 125

Gln Lys Ile Phe Asp Leu Arg Gly Lys Phe Lys Arg Pro Thr Leu Arg
            130                 135                 140

Arg Val Arg Ile Ser Ala Asp Ala Met
145                 150
```

(2) INFORMATION FOR SEQ ID NO:4:

(i) SEQUENCE CHARACTERISTICS:
        (A) LENGTH: 211 amino acids
        (B) TYPE: amino acid
        (C) STRANDEDNESS: single
        (D) TOPOLOGY: linear (xi) SEQUENCE DESCRIPTION: SEQ ID NO:4:

```
Met Ala Asp Gly Ser Ser Asp Ala Ala Arg Glu Pro Arg Pro Ala Pro
1               5                   10                  15

Ala Pro Ile Arg Arg Arg Ser Ser Asn Tyr Arg Ala Tyr Ala Thr Glu
            20                  25                  30
```

```
Pro His Ala Lys Lys Ser Lys Ile Ser Ala Ser Arg Lys Leu Gln
        35              40                  45

Leu Lys Thr Leu Leu Leu Gln Ile Ala Lys Gln Glu Leu Glu Arg Glu
    50              55                  60

Ala Glu Glu Arg Arg Gly Glu Lys Gly Arg Ala Leu Ser Thr Arg Cys
65              70                  75                  80

Gln Pro Leu Glu Leu Thr Gly Leu Gly Phe Ala Glu Leu Gln Asp Leu
                85                  90                  95

Cys Arg Gln Leu His Ala Arg Val Asp Lys Val Asp Glu Glu Arg Tyr
                100                 105                 110

Asp Ile Glu Ala Lys Val Thr Lys Asn Ile Thr Glu Ile Ala Asp Leu
                115                 120                 125

Thr Gln Lys Ile Phe Asp Leu Arg Gly Lys Phe Lys Arg Pro Thr Leu
    130                 135                 140

Arg Arg Val Arg Ile Ser Ala Asp Ala Met Met Gln Ala Leu Leu Gly
145                 150                 155                 160

Ala Arg Ala Lys Glu Ser Leu Asp Leu Arg Ala His Leu Lys Gln Val
                165                 170                 175

Lys Lys Glu Asp Thr Glu Lys Glu Asn Arg Glu Val Gly Asp Trp Arg
                180                 185                 190

Lys Asn Ile Asp Ala Leu Ser Gly Met Glu Gly Arg Lys Lys Lys Phe
                195                 200                 205

Glu Ser Pro
    210

(2) INFORMATION FOR SEQ ID NO:5:

(i) SEQUENCE CHARACTERISTICS:
        (A) LENGTH: 3 amino acids
        (B) TYPE:amino acid
        (C) STRANDEDNESS: single
        (D) TOPOLOGY: linear (xi) SEQUENCE DESCRIPTION: SEQ ID NO:5:

Ala Ser Met
1

(2) INFORMATION FOR SEQ ID NO:6:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:6:

Thr Leu Trp Met
1

(2) INFORMATION FOR SEQ ID NO:7:

(i) SEQUENCE CHARACTERISTICS:
        (A) LENGTH: 46 amino acids
        (B) TYPE: amino acid
        (C) STRANDEDNESS: single
        (D) TOPOLOGY: linear (xi) SEQUENCE DESCRIPTION: SEQ ID NO:7:

Gln Ala Leu Leu Gly Ala Arg Ala Lys Gly Ser Leu Asp Leu Arg Ala
1               5                   10                  15

His Leu Lys Gln Val Lys Lys Glu Asp Thr Glu Lys Glu Asn Arg Glu
```

```
                        20                  25                  30
Val Gly Asp Trp Arg Lys Asn Ile Asp Ala Leu Ser Gly Met
            35                  40                  45
```

(2) INFORMATION FOR SEQ ID NO:8:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:8:

```
Glu Gly Arg Lys Lys Lys Phe Glu Ser Pro Met
1               5                   10
```

(2) INFORMATION FOR SEQ ID NO:9:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:9:

```
Val His His His His His His
1               5
```

(2) INFORMATION FOR SEQ ID NO:10:

(i) SEQUENCE CHARACTERISTICS:
        (A) LENGTH: 88 amino acids
        (B) TYPE: amino acid
        (C) STRANDEDNESS: single
        (D) TOPOLOGY: linear (xi) SEQUENCE DESCRIPTION: SEQ ID NO:10:

```
Asp Ala Ala Arg Glu Pro Arg Pro Ala Pro Ala Pro Ile Arg Arg Arg
1               5                   10                  15

Ser Ser Asn Tyr Arg Ala Tyr Ala Thr Glu Pro His Ala Lys Lys Lys
            20                  25                  30

Ser Lys Ile Ser Ala Ser Arg Lys Leu Gln Leu Lys Thr Leu Leu Leu
            35                  40                  45

Gln Ile Ala Lys Gln Glu Leu Glu Arg Glu Ala Glu Glu Arg Arg Gly
    50                  55                  60

Glu Lys Gly Arg Ala Leu Ser Thr Arg Cys Gln Pro Leu Glu Leu Thr
65                  70                  75                  80

Gly Leu Gly Phe Ala Glu Leu Gln
                85
```

We claim:

1. An isolated fragment of human cardiac TnI comprising the following sequence

X-A-B-Y wherein

X comprises any of amino acid residues 1–27 of SEQ ID NO: 2;

A comprises amino acid residues 28–69 of SEQ ID NO: 2;

B comprises amino acid residues 70–90 of SEQ ID NO: 2;

and Y comprises any of amino residues 91–170 of SEQ ID NO: 2.

2. The isolated fragment of claim 1, wherein X is selected from the group of amino acid residues consisting of 1–27, 2–27, 4–27, 6–27, 10–27, 15–27, 20–27, 25–27, and 27 of SEQ ID NO: 2.

3. The isolated fragment of claim 1, wherein X is selected from the group of amino acid residues consisting of 1–27, 2–27, 3–27, 4–27, 5–27, 6–27, 7–27, 8–27, 9–27, 10–27, 15–27, 20–27, 21–27, 22–27, 23–27, 24–27, 25–27, 26–27, and 27 of SEQ ID NO: 2.

4. The isolated fragment of claim 1, wherein Y is selected from the group of amino acid residues consisting of 91–95, 91–100, 91–105, 91–110, 91–115, 91–120, 91–130, 91–140, 91–145, 91–150, 91–153, 91–155, 91–160, 91–165, and 91–170 of SEQ ID NO 2.

5. The isolated fragment of claim 1, wherein Y is selected from the group of amino acid residues consisting of 91–92, 91–93, 91–94, 91–95, 91–96, 91–97, 91–98, 91–99, 91–100, 91–105, 91–110, 91–115, 91–116, 91–117, 91–118, 91–119, 91–120, 91–121, 91–122, 91–123, 91–124, 91–125, 91–126, 91–127, 91–128, 91–129, 91–130, 91–131, 91–132, 91–133, 91–134, 91–135, 91–136, 91–137, 91–138, 91–139, 91–140, 91–141, 91–142, 91–143, 91–144, 91–145, 91–146, 91–147, 91–148, 91–149, 91–150, 91–151, 91–152, 91–153, 91–154, 91–155, 91–160, 91–165, and 91–170 of SEQ ID NO: 2.

6. The fragment according to claim 1, wherein X comprises residues 1–27, 6–27, or 27 of SEQ ID NO: 2 and Y comprises any of residues 91–95, 91–120, 91–121, 91–122, 91–123, 91–124, 91–125, 91–126, 91–127, 91–128, 91–129, 91–130, 91–131, 91–132, 91–133, 91–134, 91–135, 91–136, 91–137, 91–138, 91–139, 91–140, 91–141, 91–142, 91–143, 91–144, 91–145, or 91–153 of SEQ ID NO: 2.

7. The fragment according to claim 1, wherein X comprises residues 1–27 and Y comprises any of 91–135, 91–136, 91–137, 91–138, 91–139, 91–140, 91–141, 91–142, 91–143, 91–144, 91–145, or 91–153 of SEQ ID NO: 2.

8. The fragment according to claim 1, wherein the fragment has a greater immunological reactivity than intact cTnI when the fragment and intact cTnI are reacted with a monoclonal antibody which has an epitopic site on the fragment.

9. The fragment according to claim 1, wherein the fragment has an immunological reactivity at least two times greater than intact cTnI when the fragment and intact cTnI are reacted with a monoclonal antibody which has an epitopic site on the fragment.

10. The fragment according to claim 1, wherein the fragment has an apparent molecular weight of 14,000.

11. The fragment according to claim 1, wherein the fragment comprises the binding site for TnC.

12. A calibrator for a TnI immunoassay comprising:
a) a known amount of the fragment of claim 1; and
b) serum or calibrator base.

13. The calibrator according to claim 12, wherein the calibrator base comprises a buffer containing BSA.

14. A control for a TnI immunoassay comprising:
a) a known amount of the fragment of claim 1; and
b) serum or control base.

15. The control according to claim 14 wherein the control base comprises a buffer containing BSA.

16. An isolated fragment of human cardiac TnI polypeptide, comprising a sequence of amino acids having amino acid residues 27–91 of SEQ ID NO: 2.

17. An isolated fragment of human cardiac TnI polypeptide according to claim 16, wherein the polypeptide has a greater immunological reactivity than intact TnI when reacted with a monoclonal antibody that binds to an epitopic site on TnI.

18. A calibrator for a TnI immunoassay comprising:
a) a known amount of the fragment of claim 16; and
b) serum or calibrator base.

19. A calibrator according to claim 18, wherein the calibrator base comprises a buffer containing BSA.

20. A control for a TnI immunoassay, comprising:
a) a known amount of the fragment of claim 16; and
b) serum or control base.

21. A control according to claim 20, wherein the control base comprises a buffer containing BSA.

* * * * *